United States Patent [19]
Hoo

[11] Patent Number: 5,891,432
[45] Date of Patent: Apr. 6, 1999

[54] MEMBRANE-BOUND CYTOKINE COMPOSITIONS COMPRISING GM=CSF AND METHODS OF MODULATING AN IMMUNE RESPONSE USING SAME

[75] Inventor: William Soo Hoo, Carlsbad, Calif.

[73] Assignee: The Immune Response Corporation, Carlsbad, Calif.

[21] Appl. No.: 902,516

[22] Filed: Jul. 29, 1997

[51] Int. Cl.$^6$ .................................................. A61K 48/00
[52] U.S. Cl. .................. 424/93.21; 424/93.2; 424/192.1; 424/85.1; 435/69.7; 435/325; 435/252.3; 530/351; 536/23.4
[58] Field of Search ............................... 424/93.21, 93.2, 424/192.1, 85.1; 435/69.5, 69.51, 69.7, 325, 360, 365.1, 252.3; 530/351; 536/23.4

[56] References Cited

U.S. PATENT DOCUMENTS

| | | | |
|---|---|---|---|
| 5,109,113 | 4/1992 | Caras et al. ............................... | 530/350 |
| 5,616,477 | 4/1997 | Price ....................................... | 435/69.5 |
| 5,637,483 | 6/1997 | Dranoff et al. ......................... | 424/93.21 |
| 5,662,907 | 9/1997 | Kubo et al. ............................. | 424/184.1 |
| 5,759,535 | 6/1998 | Cohen .................................... | 424/93.21 |

FOREIGN PATENT DOCUMENTS

| | | |
|---|---|---|
| WO 97/15669 | 5/1997 | WIPO . |
| WO 97/20048 | 6/1997 | WIPO . |
| 98/06746 | 2/1998 | WIPO . |

OTHER PUBLICATIONS

H. Büeler et al., Molecular Medicine 2(5):545–555, Sep. 1996.
Belardelli, "Role of Interferons and Other Cytokines in the Regulation of the Immune Response," *APMIS* 105:161–179 (1995).
Blachere and Srivastava, "Heat Shock Protein–Based Cancer Vaccines and Related Thoughts on Immunogenicity of Human Tumors," *Seminars in Cancer Biology* 6:349–355 (1995).
Dranoff et al., "Vaccination With Irradiated Tumor Cells Engineered to Secrete Murine Granulocyte–Macrophage Colony–Stimulating Factor Stimulates Potent, Specific, and Long–Lasting Anti–Tumor Immunity," *Proc. Natl. Acad. Sci., USA* 90:3539–3543 (1993).
Francisco and Georgiou, "The Expression of Recombinant Proteins on the External Surface of *Escherichia coli,*" *Ann NY Acad Sci.* 745:372–382 (1994).
Fan et al., "The Proinflammatory Cytokine Interleukin–12 Occurs as a Cell Membrane–Bound Form on Macrophages," *Biochem. Biophys. Research Comm.* 225:1063–1067 (1996).
Hakim et al., "A Nine–Amino Acid Peptide From IL–1β Augments Antitumor Immune Responses Induced by Protein and DNA Vaccines," *The Journal of Immunology* 157:5503–5511 (1996).
Jadus et al., "Macrophages Can Recogize and Kill Tumor Cells Bearing the Membrane Isoform of Macrophage Colony–Stimulating Factor," *Blood* 87:5232–5241 (1996).
Lukacs et al., "Tumor Cells Transfected with a Bacterial Heat–Shock Gene Lose Tumorigenicity and Induce Protection Against Tumors," *J. Exp. Med.* 178:343–348 (1993).

Murphy and vanderSpek, "Targeting Diphtheria Toxin to Growth Factor Receptors," *Seminars in Cancer Biology* 6:259–267 (1995).
Musiani et al., "Cytokines, Tumour–Cell Death and Immunogenicity: A Question of Choice," *Immunology Today* 18:27–31 (1997).
Ni and O'Neill, "The Role of Dendritic Cell in T Cell Activation," *Immunology and Cell Biology* 75:223–230 (1997).
Pardoll, "Paracrine Cytokine Adjuvants in Cancer Immunotherapy," *Ann. Rev. Immunol.* 13:399–415 (1995).
Perez et al., "A Nonsecretable Cell Surface Mutant of Tumor Necrosis Factor (TNF) Kills by Cell–to–Cell Contact," *Cell* 63:251–258 (1990).
Robbins and Kawakami, "Human Tumor Antigens Recognized by T Cells," *Curr. Opin. in Immunology* 8:628–636 (1996).
Sasaki et al., "Cell–to–Cell Interaction of Cytokine–Dependent Myeloblastic Line Constitutively Expressing Membrane–Bound Stem Cell Factor Abrogates Cytokine Dependency Partially Through Granulocyte–Macrophage Colony–Stimulating Factor Production," *Blood* 85:1220–1228 (1995).
Schmidt–Wolf and Schmidt–Wolf, "Cytokines and Gene Therapy," *Immunology Today* 16:173–175 (1995).
Silva et al., "Characterization of T Cells that Confer a High Degree of Protective Immunity Against Tuberculosis in Mice After Vaccination With Tumor Cells Expressing Mycobacterial hsp65," *Infection and Immunity* 64:2400–2407 (1996).
Steinman, "Dendritic Cells and Immune–Based Therapies," *Exper. Hematol.* 24:859–862 (1996).
Tao and Levy, "Idiotype/Granulocyte–Macrophage Colony Stimulating Factor Fusion Protein as a Vaccine for B–cell Lymphoma," *Nature* 362:755–758 (1993).
Tepper and Mulé, "Experimental and Clinical Studies of Cytokine Gene–Modified Tumor Cells," *Human Gene Therapy* 5:153–164 (1994).

*Primary Examiner*—Lorraine Spector
*Attorney, Agent, or Firm*—Campbell & Flores LLP

[57] ABSTRACT

The present invention provides a cellular vaccine having a membrane-bound fusion protein that includes a non-antibody immunomodulatory molecule such as GM-CSF operatively fused to a heterologous membrane attachment domain. Non-antibody immunomodulatory molecules useful in the invention include immunostimulatory and immunosuppressive molecules such as cytokines. In one embodiment, the invention provides a cellular vaccine having a membrane-bound fusion protein that includes a non-antibody immunomodulatory molecule operatively fused to a heterologous membrane attachment domain and, additionally, a disease-associated antigen or immunogenic epitope thereof. Further provided by the invention are methods of modulating an immune response against a disease-associated antigen by administering to an individual a cellular vaccine having a membrane-bound fusion protein that includes a non-antibody immunomodulatory molecule operatively fused to a heterologous membrane attachment domain.

24 Claims, 7 Drawing Sheets

```
            10         20         30         40         50
         *    *    *    *    *    *    *    *    *    *
        ATGGAGACAG ACACACTCCT GCTATGGGTA CTGCTGCTCT GGGTTCCAGG
         M  E  T   D  T  L  L  L  W  V   L  L  L    W  V  P  G
        |——————— murine kappa light chain signal sequence ———————
            60         70         80         90        100
         *    *    *    *    *    *    *    *    *    *
        TTCCACTGGT GACTATCCAT ATGATGTTCC AGATTATGCT GGGGCCCAAG
         S  T  G   D  Y  P    Y  D  V  P  D  Y  A   G  A  Q
                                                              ──▶
           110        120        130        140        150
         *    *    *    *    *    *    *    *    *    *
        CACCCACCCG CTCACCCATC ACTGTCACCC GGCCTTGGAA GCATGTAGAG
         A  P  T  R  S  P  I   T  V  T   R  P  W  K  H  V  E
        |——————— mouse GMCSF ———————
           160        170        180        190        200
         *    *    *    *    *    *    *    *    *    *
        GCCATCAAAG AAGCCCTGAA CCTCCTGGAT GACATGCCTG TCACGTTGAA
         A  I  K   E  A  L  N  L  L  D   D  M  P    V  T  L  N 210        220        230        240        250
         *    *    *    *    *    *    *    *    *    *
        TGAAGAGGTA GAAGTCGTCT CTAACGAGTT CTCCTTCAAG AAGCTAACAT
         E  E  V   E  V  V    S  N  E  F  S  F  K   K  L  T 260        270        280        290        300
         *    *    *    *    *    *    *    *    *    *
        GTGTGCAGAC CCGCCTGAAG ATATTCGAGC AGGGTCTACG GGGCAATTTC
         C  V  Q  T  R  L  K  I  F  E   Q  G  L  R  G  N  F 310        320        330        340        350
         *    *    *    *    *    *    *    *    *    *
        ACCAAACTCA AGGGCGCCTT GAACATGACA GCCAGCTACT ACCAGACATA
         T  K  L   K  G  A  L  N  M  T   A  S  Y    Y  Q  T  Y
```

FIG. 2A

```
        360         370         380         390         400
         *           *           *           *           *
CTGCCCCCCA  ACTCCGGAAA  CGGACTGTGA  AACACAAGTT  ACCACCTATG
  C  P  P    T  P  E    T  D  C  E   T  Q  V    T  T  Y 410         420         430         440         450
         *           *           *           *           *
CGGATTTCAT  AGACAGCCTT  AAAACCTTTC  TGACTGATAT  CCCCTTTGAA
A  D  F  I   D  S  L    K  T  F    L  T  D  I   P  F  E 460         470         480         490         500
         *           *           *           *           *
TGCAAAAAAC  CAGGCCAAAA  AGTCGACGAA  CAAAAACTCA  TCTCAGAAGA
 C  K  K    P  G  Q  K   V  D  E    Q  K  L    I  S  E  E
——— mouse GMCSF ———▶|
        510         520         530         540         550
         *           *           *           *           *
GGATCTGAAT  GCTGTGGGCC  AGGACACGCA  GGAGGTCATC  GTGGTGCCAC
 D  L  N    A  V  G     Q  D  T  Q   E  V  I    V  V  P 560         570         580         590         600
         *           *           *           *           *
ACTCCTTGCC  CTTTAAGGTG  GTGGTGATCT  CAGCCATCCT  GGCCCTGGTG
 H  S  L  P  F  K  V    V  V  I     S  A  I  L   A  L  V
            |◀——— PDGFRβ transmembrane domain... ———
        610         620         630         640         650
         *           *           *           *           *
GTGCTCACCA  TCATCTCCCT  TATCATCCTC  ATCATGCTTT  GGCAGAAGAA
 V  L  T    I  I  S  L   I  I  L    I  M  L    W  Q  K  K
transmembrane domain ———————————————————————————————————
        660         670         680         690
         *           *           *           *           *
GCCACGTTAG  GCGGCCGCTC  GAGATCAGCC  TCGACTGTGC  CTTCTAG
 P  R  *    A  A  A     R  D  Q  P   R  L  C    L  L
———————▶|
```

FIG. 2B

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:

(A) LENGTH: 660 base pairs
(B) TYPE: nucleic acid
(C) STRANDEDNESS: both
(D) TOPOLOGY: linear (ix) FEATURE:
(A) NAME/KEY: CDS
(B) LOCATION: 1..660

(xi) SEQUENCE DESCRIPTION: SEQ ID NO:1:

| ATG | GAG | ACA | GAC | ACA | CTC | CTG | CTA | TGG | GTA | CTG | CTG | CTC | TGG | GTT | CCA | 48 |
| Met | Glu | Thr | Asp | Thr | Leu | Leu | Leu | Trp | Val | Leu | Leu | Leu | Trp | Val | Pro | |
| 1 | | | | 5 | | | | | 10 | | | | | 15 | | |

| GGT | TCC | ACT | GGG | GAC | TAT | CCA | TAT | GAT | GTT | CCA | GAT | TAT | GCT | GGG | GCC | 96 |
| Gly | Ser | Thr | Gly | Asp | Tyr | Pro | Tyr | Asp | Val | Pro | Asp | Tyr | Ala | Gly | Ala | |
| | | | 20 | | | | | 25 | | | | | 30 | | | |

| CAA | GCA | CCC | ACC | CGC | TCA | CCC | ATC | ACT | GTC | ACC | CGG | CCT | TGG | AAG | CAT | 144 |
| Gln | Ala | Pro | Thr | Arg | Ser | Pro | Ile | Thr | Val | Thr | Arg | Pro | Trp | Lys | His | |
| | | 35 | | | | | 40 | | | | | 45 | | | | |

| GTA | GAG | GCC | ATC | AAA | GAA | GCC | CTG | AAC | CTC | CTG | GAT | GAC | ATG | CCT | GTC | 192 |
| Val | Glu | Ala | Ile | Lys | Glu | Ala | Leu | Asn | Leu | Leu | Asp | Asp | Met | Pro | Val | |
| | 50 | | | | | 55 | | | | | 60 | | | | | |

| ACG | TTG | AAT | GAA | GAG | GTA | GAA | GTC | GTC | TCT | AAC | GAG | TTC | TCC | TTC | AAG | 240 |
| Thr | Leu | Asn | Glu | Glu | Val | Glu | Val | Val | Ser | Asn | Glu | Phe | Ser | Phe | Lys | |
| 65 | | | | | 70 | | | | | 75 | | | | | 80 | |

| AAG | CTA | ACA | TGT | GTG | CAG | ACC | CGC | CTG | AAG | ATA | TTC | GAG | CAG | GGT | CTA | 288 |
| Lys | Leu | Thr | Cys | Val | Gln | Thr | Arg | Leu | Lys | Ile | Phe | Glu | Gln | Gly | Leu | |
| | | | | 85 | | | | | 90 | | | | | 95 | | |

| CGG | GGC | AAT | TTC | ACC | AAA | CTC | AAG | GGC | GCC | TTG | AAC | ATG | ACA | GCC | AGC | 336 |
| Arg | Gly | Asn | Phe | Thr | Lys | Leu | Lys | Gly | Ala | Leu | Asn | Met | Thr | Ala | Ser | |
| | | | 100 | | | | | 105 | | | | | 110 | | | |

| TAC | TAC | CAG | ACA | TAC | TGC | CCC | CCA | ACT | CCG | GAA | ACG | GAC | TGT | GAA | ACA | 384 |
| Tyr | Tyr | Gln | Thr | Tyr | Cys | Pro | Pro | Thr | Pro | Glu | Thr | Asp | Cys | Glu | Thr | |
| | | 115 | | | | | 120 | | | | | 125 | | | | |

| CAA | GTT | ACC | ACC | TAT | GCG | GAT | TTC | ATA | GAC | AGC | CTT | AAA | ACC | TTT | CTG | 432 |
| Gln | Val | Thr | Thr | Tyr | Ala | Asp | Phe | Ile | Asp | Ser | Leu | Lys | Thr | Phe | Leu | |
| | 130 | | | | | 135 | | | | | 140 | | | | | |

| ACT | GAT | ATC | CCC | TTT | GAA | TGC | AAA | AAA | CCA | GGC | CAA | AAA | GTC | GAC | GAA | 480 |
| Thr | Asp | Ile | Pro | Phe | Glu | Cys | Lys | Lys | Pro | Gly | Gln | Lys | Val | Asp | Glu | |
| 145 | | | | | 150 | | | | | 155 | | | | | 160 | |

| CAA | AAA | CTC | ATC | TCA | GAA | GAG | GAT | CTG | AAT | GCT | GTG | GGC | CAG | GAC | ACG | 528 |
| Gln | Lys | Leu | Ile | Ser | Glu | Glu | Asp | Leu | Asn | Ala | Val | Gly | Gln | Asp | Thr | |
| | | | | 165 | | | | | 170 | | | | | 175 | | |

| CAG | GAG | GTC | ATC | GTG | GTG | CCA | CAC | TCC | TTG | CCC | TTT | AAG | GTG | GTG | GTG | 576 |
| Gln | Glu | Val | Ile | Val | Val | Pro | His | Ser | Leu | Pro | Phe | Lys | Val | Val | Val | |
| | | | 180 | | | | | 185 | | | | | 190 | | | |

| ATC | TCA | GCC | ATC | CTG | GCC | CTG | GTG | GTG | CTC | ACC | ATC | ATC | TCC | CTT | ATC | 624 |
| Ile | Ser | Ala | Ile | Leu | Ala | Leu | Val | Val | Leu | Thr | Ile | Ile | Ser | Leu | Ile | |
| | | 195 | | | | | 200 | | | | | 205 | | | | |

| ATC | CTC | ATC | ATG | CTT | TGG | CAG | AAG | AAG | CCA | CGT | TAG | | | | | 660 |
| Ile | Leu | Ile | Met | Leu | Trp | Gln | Lys | Lys | Pro | Arg | | | | | | |
| | 210 | | | | | 215 | | | | | 220 | | | | | |

(2) INFORMATION FOR SEQ ID NO:2:

(i) SEQUENCE CHARACTERISTICS:
(A) LENGTH: 219 amino acids
(B) TYPE: amino acid
(D) TOPOLOGY: linear (ii) MOLECULE TYPE: protein (xi) SEQUENCE DESCRIPTION: SEQ ID NO:2:

Met Glu Thr Asp Thr Leu Leu Leu Trp Val Leu Leu Leu Trp Val Pro

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Gly | Ser | Thr | Gly | Asp | Tyr | Pro | Tyr | Asp | Val | Pro | Asp | Tyr | Ala | Gly | Ala |
|  |  |  | 20 |  |  |  |  | 25 |  |  |  | 30 |  |  |
| Gln | Ala | Pro | Thr | Arg | Ser | Pro | Ile | Thr | Val | Thr | Arg | Pro | Trp | Lys | His |
|  |  | 35 |  |  |  |  | 40 |  |  |  |  | 45 |  |  |
| Val | Glu | Ala | Ile | Lys | Glu | Ala | Leu | Asn | Leu | Leu | Asp | Asp | Met | Pro | Val |
|  | 50 |  |  |  |  | 55 |  |  |  | 60 |  |  |  |  |
| Thr | Leu | Asn | Glu | Glu | Val | Glu | Val | Val | Ser | Asn | Glu | Phe | Ser | Phe | Lys |
| 65 |  |  |  |  | 70 |  |  |  | 75 |  |  |  |  |  | 80 |
| Lys | Leu | Thr | Cys | Val | Gln | Thr | Arg | Leu | Lys | Ile | Phe | Glu | Gln | Gly | Leu |
|  |  |  |  | 85 |  |  |  |  | 90 |  |  |  |  | 95 |  |
| Arg | Gly | Asn | Phe | Thr | Lys | Leu | Lys | Gly | Ala | Leu | Asn | Met | Thr | Ala | Ser |
|  |  |  | 100 |  |  |  |  | 105 |  |  |  | 110 |  |  |  |
| Tyr | Tyr | Gln | Thr | Tyr | Cys | Pro | Pro | Thr | Pro | Glu | Thr | Asp | Cys | Glu | Thr |
|  |  |  | 115 |  |  |  | 120 |  |  |  |  | 125 |  |  |  |
| Gln | Val | Thr | Thr | Tyr | Ala | Asp | Phe | Ile | Asp | Ser | Leu | Lys | Thr | Phe | Leu |
|  |  | 130 |  |  |  |  | 135 |  |  |  | 140 |  |  |  |  |
| Thr | Asp | Ile | Pro | Phe | Glu | Cys | Lys | Lys | Pro | Gly | Gln | Lys | Val | Asp | Glu |
| 145 |  |  |  |  | 150 |  |  |  |  | 155 |  |  |  |  | 160 |
| Gln | Lys | Leu | Ile | Ser | Glu | Glu | Asp | Leu | Asn | Ala | Val | Gly | Gln | Asp | Thr |
|  |  |  |  | 165 |  |  |  |  | 170 |  |  |  |  | 175 |  |
| Gln | Glu | Val | Ile | Val | Val | Pro | His | Ser | Leu | Pro | Phe | Lys | Val | Val | Val |
|  |  |  | 180 |  |  |  |  | 185 |  |  |  |  | 190 |  |  |
| Ile | Ser | Ala | Ile | Leu | Ala | Leu | Val | Val | Leu | Thr | Ile | Ile | Ser | Leu | Ile |
|  |  | 195 |  |  |  |  | 200 |  |  |  |  | 205 |  |  |  |
| Ile | Leu | Ile | Met | Leu | Trp | Gln | Lys | Lys | Pro | Arg |  |  |  |  |  |
| 210 |  |  |  |  |  | 215 |  |  |  |  |  |  |  |  |  |

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

| Val | Gln | Gly | Glu | Glu | Ser | Asn | Asp | Lys |
|---|---|---|---|---|---|---|---|---|
| 1 |  |  |  | 5 |  |  |  |  |

( 2 ) INFORMATION FOR SEQ ID NO:4:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

| Phe | Ile | Leu | Pro | Ile | Leu | Gly | Ala | Val | Leu | Ala | Leu | Leu | Leu | Leu | Leu |
|---|---|---|---|---|---|---|---|---|---|---|---|---|---|---|---|
| 1 |  |  |  | 5 |  |  |  |  | 10 |  |  |  |  | 15 |  |
| Thr | Leu | Leu | Ala | Leu | Leu | Leu | Leu | Val |  |  |  |  |  |  |  |
|  |  |  | 20 |  |  |  |  | 25 |  |  |  |  |  |  |  |

( 2 ) INFORMATION FOR SEQ ID NO:5:

( i ) SEQUENCE CHARACTERISTICS:
        ( A ) LENGTH: 26 amino acids
        ( B ) TYPE: amino acid -continued (D) TOPOLOGY: linear (ii) MOLECULE TYPE: peptide (xi) SEQUENCE DESCRIPTION: SEQ ID NO:5:

| Ile | Tyr | Leu | Ile | Ile | Gly | Ile | Cys | Gly | Gly | Gly | Ser | Leu | Leu | Met | Val |
|---|---|---|---|---|---|---|---|---|---|---|---|---|---|---|---|
| 1 | | | | 5 | | | | | 10 | | | | | 15 | |
| Phe | Val | Ala | Leu | Leu | Val | Phe | Tyr | Ile | Thr | | | | | | |
| | | | 20 | | | | | 25 | | | | | | | |

(2) INFORMATION FOR SEQ ID NO:6:

(i) SEQUENCE CHARACTERISTICS:
(A) LENGTH: 22 amino acids
(B) TYPE: amino acid
(D) TOPOLOGY: linear (ii) MOLECULE TYPE: peptide (xi) SEQUENCE DESCRIPTION: SEQ ID NO:6:

| Ala | Leu | Val | Val | Ile | Pro | Ile | Ile | Phe | Gly | Ile | Leu | Phe | Ala | Ile | Leu |
|---|---|---|---|---|---|---|---|---|---|---|---|---|---|---|---|
| 1 | | | | 5 | | | | | 10 | | | | | 15 | |
| Leu | Val | Leu | Val | Phe | Ile | | | | | | | | | | |
| | | | | 20 | | | | | | | | | | | |

(2) INFORMATION FOR SEQ ID NO:7:

(i) SEQUENCE CHARACTERISTICS:
(A) LENGTH: 20 amino acids
(B) TYPE: amino acid
(D) TOPOLOGY: linear (ii) MOLECULE TYPE: peptide (xi) SEQUENCE DESCRIPTION: SEQ ID NO:7:

| Ile | Ser | Gly | Ala | Thr | Ala | Gly | Val | Pro | Thr | Leu | Leu | Leu | Gly | Leu | Val |
|---|---|---|---|---|---|---|---|---|---|---|---|---|---|---|---|
| 1 | | | | 5 | | | | | 10 | | | | | 15 | |
| Leu | Pro | Ala | Pro | | | | | | | | | | | | |
| | | | 20 | | | | | | | | | | | | |

(2) INFORMATION FOR SEQ ID NO:8:

(i) SEQUENCE CHARACTERISTICS:
(A) LENGTH: 24 amino acids
(B) TYPE: amino acid
(D) TOPOLOGY: linear (ii) MOLECULE TYPE: peptide (xi) SEQUENCE DESCRIPTION: SEQ ID NO:8:

| Leu | Leu | Leu | Gly | Val | Ser | Val | Ser | Cys | Ile | Val | Ile | Leu | Ala | Val | Cys |
|---|---|---|---|---|---|---|---|---|---|---|---|---|---|---|---|
| 1 | | | | 5 | | | | | 10 | | | | | 15 | |
| Leu | Leu | Cys | Tyr | Val | Ser | Ile | Thr | | | | | | | | |
| | | | 20 | | | | | | | | | | | | |

(2) INFORMATION FOR SEQ ID NO:9:

(i) SEQUENCE CHARACTERISTICS:
(A) LENGTH: 24 amino acids
(B) TYPE: amino acid
(D) TOPOLOGY: linear (ii) MOLECULE TYPE: peptide (xi) SEQUENCE DESCRIPTION: SEQ ID NO:9:

| Val | Ala | Gly | Val | Val | Ile | Ile | Val | Ile | Leu | Leu | Ile | Leu | Thr | Gly | Ala |
|---|---|---|---|---|---|---|---|---|---|---|---|---|---|---|---|
| 1 | | | | 5 | | | | | 10 | | | | | 15 | |

```
Gly  Leu  Ala  Ala  Tyr  Phe  Phe  Tyr
              20
```

( 2 ) INFORMATION FOR SEQ ID NO:10:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Phe  Leu  Phe  Thr  Pro  Val  Val  Val  Ala  Cys  Met  Ser  Ile  Met  Ala  Leu
1                   5                        10                       15
Leu  Leu  Leu  Leu  Leu  Leu  Leu  Leu  Leu
              20                       25
```

( 2 ) INFORMATION FOR SEQ ID NO:11:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Val  Val  Val  Ile  Ser  Ala  Ile  Leu  Ala  Leu  Val  Val  Leu  Thr  Ile  Ile
1                   5                        10                       15
Ser  Leu  Ile  Ile  Leu  Ile  Met  Leu  Trp  Gln  Lys  Lys  Pro  Arg
              20                       25                       30
```

( 2 ) INFORMATION FOR SEQ ID NO:12:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Glu  Leu  Thr  Val  Ala  Ala  Ala  Val  Leu  Val  Leu  Leu  Val  Ile  Val  Ser
1                   5                        10                       15
Ile  Ser  Leu  Ile  Val  Leu  Val  Val  Thr  Trp
              20                       25
```

( 2 ) INFORMATION FOR SEQ ID NO:13:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Leu  Thr  Tyr  Phe  Gly  Gly  Ala  Val  Ala  Ser  Thr  Ile  Gly  Leu  Ile  Met
1                   5                        10                       15
Gly  Gly  Thr  Leu  Leu  Ala  Leu  Leu
              20
```

( 2 ) INFORMATION FOR SEQ ID NO:14:

( i ) SEQUENCE CHARACTERISTICS:

(A) LENGTH: 34 amino acids
(B) TYPE: amino acid
(D) TOPOLOGY: linear (ii) MOLECULE TYPE: peptide (xi) SEQUENCE DESCRIPTION: SEQ ID NO:14:

```
Val Lys Cys Gly Gly Ile Ser Leu Leu Val Gln Asn Thr Ser Trp Leu
1               5                   10                  15
Leu Leu Leu Leu Leu Ser Leu Ser Phe Leu Gln Ala Thr Asp Phe Ile
            20                  25                  30
Ser Leu
```

(2) INFORMATION FOR SEQ ID NO:15:

(i) SEQUENCE CHARACTERISTICS:
(A) LENGTH: 23 amino acids
(B) TYPE: amino acid
(D) TOPOLOGY: linear (ii) MOLECULE TYPE: peptide (xi) SEQUENCE DESCRIPTION: SEQ ID NO:15:

```
Thr Val Leu Leu Pro Leu Val Ile Phe Phe Gly Leu Cys Leu Leu Ser
1               5                   10                  15
Leu Leu Phe Ile Gly Leu Met
            20
```

(2) INFORMATION FOR SEQ ID NO:16:

(i) SEQUENCE CHARACTERISTICS:
(A) LENGTH: 23 amino acids
(B) TYPE: amino acid
(D) TOPOLOGY: linear (ii) MOLECULE TYPE: peptide (xi) SEQUENCE DESCRIPTION: SEQ ID NO:16:

```
Leu Leu Val Leu Tyr Phe Ala Ser Ser Leu Ile Ile Pro Ala Ile Gly
1               5                   10                  15
Met Ile Ile Tyr Phe Ala Arg
            20
```

(2) INFORMATION FOR SEQ ID NO:17:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:17:

```
Ile Ile Ser Ala Val Val Gly Ile Leu
1               5
```

(2) INFORMATION FOR SEQ ID NO:18:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:18:

```
Lys Ile Phe Gly Ser Leu Ala Phe Leu
```

(2) INFORMATION FOR SEQ ID NO:19:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:19:

Tyr Met Leu Asp Leu Gln Pro Glu Thr Thr
1               5                   10

(2) INFORMATION FOR SEQ ID NO:20:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:20:

Pro Asp Thr Arg Pro Ala Pro Gly Ser Thr Ala Pro Pro Ala His Gly
1               5                   10                  15
Val Thr Ser Ala
            20

(2) INFORMATION FOR SEQ ID NO:21:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:21:

Glu Ala Asp Pro Thr Gly His Ser Tyr
1               5

(2) INFORMATION FOR SEQ ID NO:22:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:22:

Ser Ala Tyr Gly Glu Pro Arg Lys Leu
1               5

(2) INFORMATION FOR SEQ ID NO:23:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:23:

Glu Val Asp Pro Ile Gly His Leu Tyr
1               5

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
Phe Leu Trp Gly Pro Arg Ala Leu Val
1               5
```

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
Ala Ala Arg Ala Val Phe Leu Ala Leu
1               5
```

( 2 ) INFORMATION FOR SEQ ID NO:26:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
Tyr Arg Pro Arg Pro Arg Arg Tyr
1               5
```

( 2 ) INFORMATION FOR SEQ ID NO:27:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
Val Leu Pro Asp Val Phe Ile Arg Cys
1               5
```

( 2 ) INFORMATION FOR SEQ ID NO:28:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

```
Ala Tyr Gly Leu Asp Phe Tyr Ile Leu
1               5
```

( 2 ) INFORMATION FOR SEQ ID NO:29:

( i ) SEQUENCE CHARACTERISTICS:
        ( A ) LENGTH: 9 amino acids ( B ) TYPE: amino acid
        ( D ) TOPOLOGY: linear ( i i ) MOLECULE TYPE: peptide ( x i ) SEQUENCE DESCRIPTION: SEQ ID NO:29:

Lys Thr Trp Gly Gln Tyr Trp Gln Val
1               5

( 2 ) INFORMATION FOR SEQ ID NO:30:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

Ile Thr Asp Gln Val Pro Phe Ser Val
1               5

( 2 ) INFORMATION FOR SEQ ID NO:31:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

Tyr Leu Glu Pro Gly Pro Val Thr Ala
1               5

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

Leu Leu Asp Gly Thr Ala Thr Leu Arg Leu
1               5                   10

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

Val Leu Tyr Arg Tyr Gly Ser Phe Ser Val
1               5                   10

( 2 ) INFORMATION FOR SEQ ID NO:34:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

Ala Ala Gly Ile Gly Ile Leu Thr Val
1               5

( 2 ) INFORMATION FOR SEQ ID NO:35:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:35:

Ile Leu Thr Val Ile Leu Gly Val Leu
1               5

( 2 ) INFORMATION FOR SEQ ID NO:36:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:36:

Met Ser Leu Gln Arg Gln Phe Leu Arg
1               5

( 2 ) INFORMATION FOR SEQ ID NO:37:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:37:

Met Leu Leu Ala Val Leu Tyr Cys Leu
1               5

( 2 ) INFORMATION FOR SEQ ID NO:38:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:38:

Tyr Met Asn Gly Thr Met Ser Gln Val
1               5

( 2 ) INFORMATION FOR SEQ ID NO:39:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:39:

Ser Glu Ile Trp Arg Asp Ile Asp Phe
1               5

( 2 ) INFORMATION FOR SEQ ID NO:40:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

Ala Phe Leu Pro Trp His Arg Leu Phe
1               5

( 2 ) INFORMATION FOR SEQ ID NO:41:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

Gln Asn Ile Leu Leu Ser Asn Ala Pro Leu Gly Pro Gln
1               5                   10

( 2 ) INFORMATION FOR SEQ ID NO:42:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

Ser Tyr Leu Gln Asp Ser Asp Pro Asp Ser Phe Gln Asp
1               5                   10

( 2 ) INFORMATION FOR SEQ ID NO:43:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

Ser Tyr Leu Asp Ser Gly Ile His Phe
1               5

( 2 ) INFORMATION FOR SEQ ID NO:44:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:

Glu Glu Lys Leu Ile Val Val Leu Phe
1               5

( 2 ) INFORMATION FOR SEQ ID NO:45:

( i ) SEQUENCE CHARACTERISTICS:
        ( A ) LENGTH: 10 amino acids (B) TYPE: amino acid
(D) TOPOLOGY: linear (ii) MOLECULE TYPE: peptide (xi) SEQUENCE DESCRIPTION: SEQ ID NO:45:

Ala Cys Asp Pro His Ser Gly His Phe Val
1               5                   10

(2) INFORMATION FOR SEQ ID NO:46:

(i) SEQUENCE CHARACTERISTICS:
    (A) LENGTH: 25 amino acids
    (B) TYPE: amino acid
    (D) TOPOLOGY: linear (ii) MOLECULE TYPE: peptide (xi) SEQUENCE DESCRIPTION: SEQ ID NO:46:

Gly Val Ser Pro Lys Val Cys Lys Asp Val Thr Val Glu Gly Ser Asn
1               5                   10                  15
Glu Phe Ala Pro Val Gln Asn Leu Thr
            20              25

(2) INFORMATION FOR SEQ ID NO:47:

(i) SEQUENCE CHARACTERISTICS:
    (A) LENGTH: 38 amino acids
    (B) TYPE: amino acid
    (D) TOPOLOGY: linear (ii) MOLECULE TYPE: peptide (xi) SEQUENCE DESCRIPTION: SEQ ID NO:47:

Gly Cys Gly Gly Ala Gly Gly Gly Gly Cys Cys Thr Ala Gly Cys
1               5                   10                  15
Ala Cys Cys Cys Ala Cys Cys Cys Gly Cys Thr Cys Ala Cys Cys Cys
                20              25                  30
Ala Thr Cys Ala Cys Thr
            35

(2) INFORMATION FOR SEQ ID NO:48:

(i) SEQUENCE CHARACTERISTICS:
    (A) LENGTH: 43 amino acids
    (B) TYPE: amino acid
    (D) TOPOLOGY: linear (ii) MOLECULE TYPE: peptide (xi) SEQUENCE DESCRIPTION: SEQ ID NO:48:

Ala Cys Cys Gly Cys Gly Gly Thr Cys Gly Ala Cys Thr Thr Thr Thr
1               5                   10                  15
Thr Gly Gly Ala Cys Thr Gly Gly Thr Thr Thr Thr Thr Gly Cys
                20              25                  30
Ala Thr Thr Cys Ala Ala Ala Gly Gly Gly Gly
            35              40

(2) INFORMATION FOR SEQ ID NO:49:

(i) SEQUENCE CHARACTERISTICS:
    (A) LENGTH: 37 base pairs
    (B) TYPE: nucleic acid
    (C) STRANDEDNESS: both
    (D) TOPOLOGY: linear (ix) FEATURE:

(A) NAME/KEY: CDS
(B) LOCATION: 1..37

(xi) SEQUENCE DESCRIPTION: SEQ ID NO:49:

| GCG | GCC | GCT | CGA | GAT | CAG | CCT | CGA | CTG | TGC | CTT | CTA | G | 37 |
|-----|-----|-----|-----|-----|-----|-----|-----|-----|-----|-----|-----|---|----|
| Ala | Ala | Ala | Arg | Asp | Gln | Pro | Arg | Leu | Cys | Leu | Leu |   |    |
| 1   |     |     |     | 5   |     |     |     |     | 10  |     |     |   |    |

(2) INFORMATION FOR SEQ ID NO:50:

(i) SEQUENCE CHARACTERISTICS:
(A) LENGTH: 12 amino acids
(B) TYPE: amino acid
(D) TOPOLOGY: linear (ii) MOLECULE TYPE: protein (xi) SEQUENCE DESCRIPTION: SEQ ID NO:50:

Ala Ala Ala Arg Asp Gln Pro Arg Leu Cys Leu Leu
1                5                    10

MEMBRANE-BOUND CYTOKINE COMPOSITIONS COMPRISING GM=CSF AND METHODS OF MODULATING AN IMMUNE RESPONSE USING SAME

BACKGROUND OF THE INVENTION

This invention relates generally to the fields of gene therapy and cellular immunotherapy and, more specifically, to immunomodulatory molecules such as cytokines expressed as membrane-bound fusion proteins.

The use of cancer cell vaccines derived from autologous cancer cells has been explored throughout this century. Unfortunately, for most patients the responses achieved with such vaccines have been at best partial and short-lived. Strategies to improve the efficacy of cancer vaccines include the use of cytokines, which are pleiotropic mediators that modulate and shape the quality and intensity of the immune response. Cytokines are occasionally autocrine or endocrine but largely paracrine hormones produced in nature by lymphocytes and monocytes. Several cytokines have been produced using recombinant DNA methodology and evaluated for their efficacy as anti-cancer therapeutics. Multiple anti-tumor activities are attributed to cytokines including (1) direct inhibition of tumor growth (α-interferon), (2) reversal of the anergy-inducing effects of tumor cells and expansion of new T-cell effectors (interleukin-2), (3) augmentation of the effector function of T cells to recognize MHC presented peptide epitopes on tumor cells (granulocyte macrophage colony stimulating factor) and (4) enhanced recruitment of cells to inflammatory sites (interleukin-4). However, many cytokines cannot be tolerated when administered at the high systemic levels required for an effective response, thus limiting the therapeutic value of these agents.

Local cytokine delivery can more closely mimic the natural immune response and avoid the toxicity associated with high systemic levels of these molecules. One approach to local cytokine delivery involves the use of genetically modified tumor cells. For example, transduction of murine tumor cells with the gene for interleukin-4 (IL-4), interleukin-2 (IL-2), interferon γ (IFN-γ), tumor necrosis factor α (TNF-α), interleukin-6 (IL-6), interleukin-7 (IL-7), granulocyte colony stimulating factor (GCSF) or granulocyte macrophage colony stimulating factor (GM-CSF) can lead to rejection of genetically modified tumor cells by syngeneic hosts. Furthermore, vaccination with cytokine-secreting cells can increase systemic immunity as well, protecting vaccinated animals from challenge with non-transduced tumor cells. Unlike systemic administration, localized cytokine transgene expression is generally not associated with toxicity.

Dendritic cells form a system of highly efficient antigen-presenting cells and are central to the design of effective anti-cancer therapies. After capturing antigen in the periphery, dendritic cells migrate to lymphoid organs and present antigens to T cells. These potent antigen-presenting cells appear unique in their ability to interact with and activate naive T cells. The potent antigen-presenting capacity of dendritic cells can be due in part to their unique life cycle and high level expression of major histocompatibility complex (MHC) class I and II molecules and co-stimulatory molecules. Granulocyte macrophage colony stimulating factor (GM-CSF) molecule is a cytokine important in the maturation and function of dendritic cells: GM-CSF binds receptors on dendritic cells and stimulates these cells to mature, present antigen and prime naive T cells. Thus, the use of GM-CSF is of particular interest in immunotherapy.

Optimal stimulation of immune cells such as dendritic cells depends upon strong cytokine-receptor interactions. Enhanced stimulation of an immune response can be achieved by increasing the number of cytokine-receptor pairings or by increasing the affinity of a cytokine-receptor interaction. However, increasing the natural affinity of cytokines for their receptors can be impractical, and available cytokine-secreting tumor cell vaccines are limited in their ability to produce a high local concentration of cytokine. Thus, there is a need for improved cellular vaccines with increased cytokine-receptor avidity.

Cellular vaccines, including membrane-bound immunostimulatory cytokines such as GM-CSF, can be used as adjuvant therapy with surgery to eliminate micro-metastases. Such cellular anti-cancer vaccines also can be administered as preventive therapy for individuals at risk for particular types of cancer, such as individuals at risk for melanoma. Conversely, vaccines including immunosuppressive cytokine molecules can be used to dampen the inappropriate immune response that causes autoimmune disorders such as rheumatoid arthritis, multiple sclerosis and psoriasis.

Thus, there is a need for improved cellular vaccines for protection against and treatment of cancers such as melanoma, colon or breast cancer; autoimmune diseases such as rheumatoid arthritis, psoriasis and multiple sclerosis; parasitic diseases; and infectious diseases such as AIDS. The present invention satisfies this need by providing improved cellular vaccines containing membrane-bound immunomodulatory molecule such as cytokines and provides related advantages as well.

SUMMARY OF THE INVENTION

The present invention provides a cellular vaccine having a membrane-bound fusion protein that includes a non-antibody immunomodulatory molecule operatively fused to a heterologous membrane attachment domain. Non-antibody immunomodulatory molecules useful in the invention include immunostimulatory and immunosuppressive molecules such as cytokines. In one embodiment, the invention provides a cellular vaccine having a membrane-bound fusion protein that includes a non-antibody immunomodulatory molecule operatively fused to a heterologous membrane attachment domain and, additionally, a disease-associated antigen or immunogenic epitope thereof. Further provided by the invention are methods of modulating an immune response against a disease-associated antigen by administering to an individual a cellular vaccine having a membrane-bound fusion protein that includes a non-antibody immunomodulatory molecule operatively fused to a heterologous membrane attachment domain.

BRIEF DESCRIPTION OF THE DRAWINGS

FIG. 2 shows the amino acid sequence (SEQ ID NO:1) and nucleotide sequence (SEQ ID NO:2) of the pHOOK™-1.GM-CSF fusion protein, which contains murine granulocyte macrophage colony stimulating factor (GM-CSF) and the human platelet derived growth factor receptor (PDGFR) β chain transmembrane domain.

DETAILED DESCRIPTION OF THE INVENTION

Figure 1A:
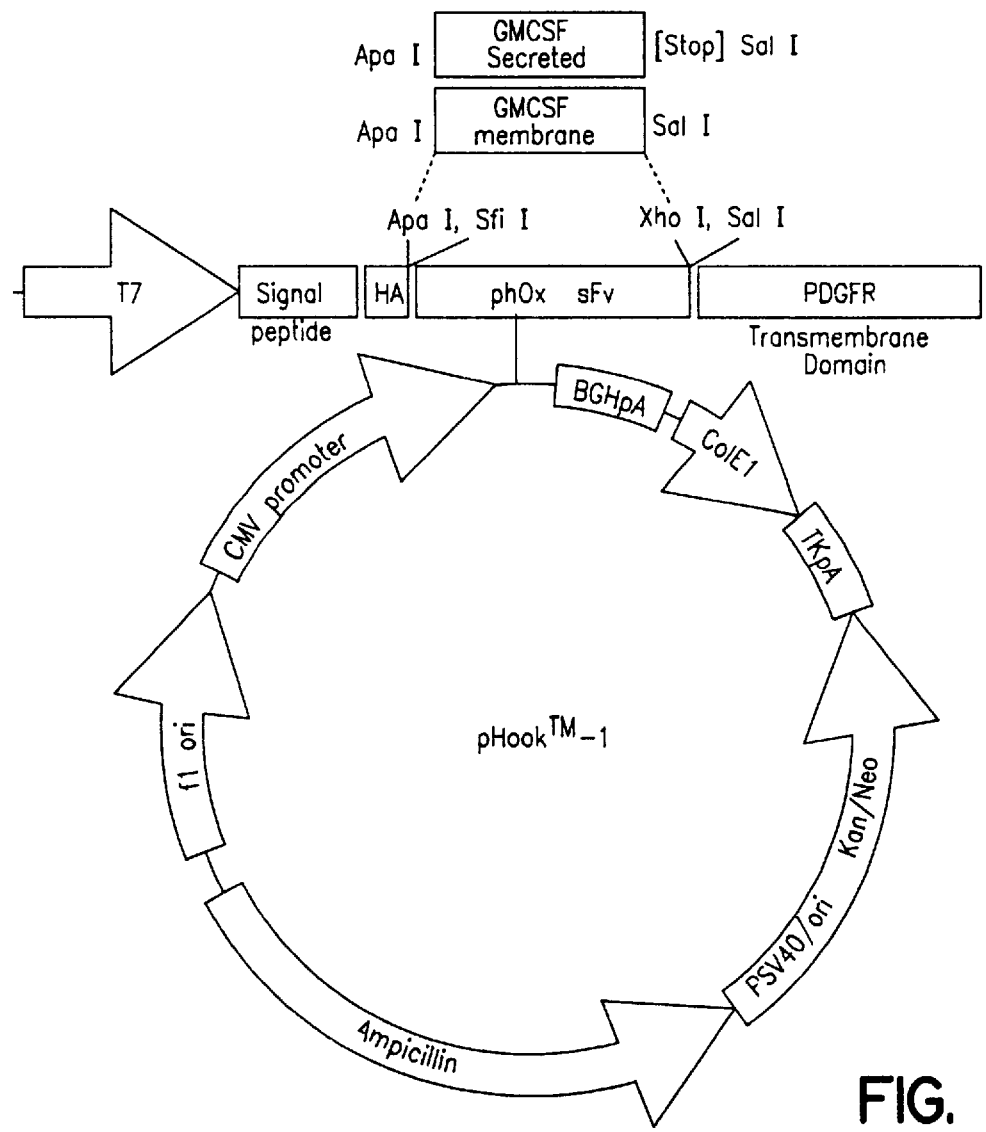
FIGS. 1A and 1B. (A) The strategy for cloning the murine GM-CSF cDNA into pHOOK™-1 is shown. (B) The resulting pHOOK™-1.GM-CSF expression vector is shown.

The present invention provides a cellular vaccine having a membrane-bound fusion protein that includes a non-antibody immunomodulatory molecule operatively fused to a heterologous membrane attachment domain. The immunomodulatory molecule can be an immunostimulatory or immunosuppressive molecule such as a cytokine. Cytokines useful in the vaccines of the invention include granulocyte macrophage colony stimulating factor (GM-CSF); granulocyte colony stimulating factor (G-CSF); interferon γ (IFN-γ); interferon α (IFN-α); tumor necrosis factor-α (TNF-α); tumor necrosis factor-β (TNF-β); interleukin-1 (IL-1); interleukin-2 (IL-2); interleukin-3 (IL-3); interleukin-4 (IL-4); interleukin-6 (IL-6); interleukin-7 (IL-7); interleukin-10 (IL-10); interleukin-12 (IL-12), lymphotactin (LTN) and dendritic cell chemokine 1 (DC-CK1).

As used herein, the term "non-antibody immunomodulatory molecule" means a molecule that modulates or regulates the production of an immune response to an antigen. A vaccine of the invention contains one or more such non-antibody immunomodulatory molecules in membrane-bound form. Antigen recognition sequences from antibody molecules are explicitly excluded from the vaccines, methods and nucleic acid molecules of the invention. As used herein, the term "antibody" means an immunoglobulin molecule or antigen-binding fragment thereof.

As used herein, the term "immunostimulatory molecule" means an immunomodulatory molecule that promotes or enhances the production of an immune response to an antigen.

As used herein, the term "immunosuppressive molecule" means an immunomodulatory molecule that reduces or inhibits the production of an immune response to an antigen.

Cytokines are immunomodulatory molecules particularly useful in the vaccines of the invention. As used herein, the term "cytokine" refers to a member of the class of proteins that are produced by cells of the immune system and that regulate or modulate an immune response. Such regulation can occur within the humoral or the cell mediated immune response and includes modulation of the effector function of T cells, B cells, NK cells macrophages, antigen presenting cells or other immune system cells.

Cytokines typically are small proteins or glycoproteins having a molecular mass of less than about 30 kDa. Although cytokines occasionally exhibit autocrine or endocrine activity, most act in a paracrine fashion and bind specific receptors on the membrane of target cells, thereby triggering signal transduction pathways that alter gene expression. Cytokines generally display very high affinity for their cognate receptors, with dissociation constants ranging from about $10^{-9}$ to $10^{-12}$M. Due to this high affinity, picomolar concentrations of cytokines can mediate biological effects. Constitutive production of cytokines is usually low or absent; cytokine expression is regulated by various inducing stimuli at the level of transcription or translation. Cytokines are typically transiently expressed with secretion lasting from a few hours to a few days (Thomson, *The Cytokine Handbook* (Second Edition) London: Harcourt Brace & Company (1994); Callard and Gearing, *The Cytokine Facts Book* Academic Press, Inc. (1994); Kuby, *Immunology* (Third Edition) New York: W.H. Freeman and Company (1997), each of which are incorporated herein by reference). Exemplary cytokines useful in the vaccines of the invention are shown in Table 1.

As used herein, the term cytokine encompasses those cytokines secreted by lymphocytes and other cell types (designated lymphokines) as well as cytokines secreted by monocytes and macrophages and other cell types (designated monokines). The term cytokine includes the interleukins, such as IL-2, IL-4 and IL-12, which are molecules secreted by leukocytes that primarily affect the growth and differentiation of hematopoietic and immune-system cells. The term cytokine also includes hematopoietic growth factors and, in particular, colony stimulating factors such as colony stimulating factor-1, granulocyte colony stimulating factor and granulocyte macrophage colony stimulating factor. In addition, the term cytokine encompasses chemokines, which are low-molecular weight molecules that mediate the chemotaxis of various leukocytes and can regulate leukocyte integrin expression or adhesion. Exemplary chemokines include interleukin-8, dendritic cell chemokine 1 (DC-CK1) and lymphotactin, which is a chemokine important for recruitment of γδ T cells and for mucosal immunity, as well as other members of the C-C and C-X-C chemokine subfamilies (see, for example, Miller and Krangel, *Crit. Rev. Immunol.* 12:17–46 (1992); Schall, "The Chemokines" in Thomson, supra, 1994; Hedrick et al., *J. Immunol.* 158:1533–1540 (1997); and Boismenu et al., *J. Immunol.* 157:985–992 (1996), each of which are incorporated herein by reference).

The term cytokine, as used herein, encompasses cytokines produced by the T helper 1 ($T_H1$) and T helper 2 ($T_H2$) subsets. Cytokines of the $T_H1$ subset are produced by $T_H1$ cells and include IL-2, IL-12, IFN-α and TNF-β. Cytokines of the $T_H1$ subset are responsible for classical cell-mediated functions such as activation of cytotoxic T lymphocytes and macrophages and delayed-type hypersensitivity. Cytokines of the $T_H1$ subset are particularly useful in stimulating an immune response to tumor cells, infected cells and intracellular pathogens.

Cytokines of the $T_H2$ subset are produced by $T_H2$ cells and include the cytokines IL-4, IL-5, IL-6 and IL-10. Cytokines of the $T_H2$ subset function effectively as helpers for B-cell activation and are particularly useful in stimulating an immune response against free living bacteria and helminthic parasites. Cytokines of the $T_H2$ subset also can mediate allergic reactions.

Active fragments of immunomodulatory molecules, for example active fragments of cytokines, also are useful in the vaccines of the invention. Such active fragments are polypeptide fragments having substantially the same amino acid sequence as a portion of the indicated immunomodulatory molecule, provided that the fragment retains at least one biological activity of the immunomodulatory molecule. Active cytokine fragments are known in the art and include, for example, a nine-amino acid peptide from IL-1β (VQGEESNDK; SEQ ID NO:3), which retains the immunostimulatory activity of the full-length IL-1β cytokine (Hakim et al., *J. Immunol.* 157:5503–5511 (1996), which is incorporated herein by reference). In addition, a variety of well known in vitro and in vivo assays for cytokine activity, such as the bone marrow proliferation assay described in Example I, are useful in testing a cytokine fragment for activity (see Thomson, supra, 1994).

TABLE 1

EXEMPLARY CYTOKINES

| Cytokine | Reference |
| --- | --- |
| Interleukin-1 (IL-1α, IL-1β) | Dinarello, Adv. Immunol. 44:153–205 (1989) |
| Interleukin-2 (IL-2) | Devos et al., Nucl. Acids Res. 11:4307–4323 (1983) |
| Interleukin-3 (IL-3) | Yang et al., Cell 47:3–10 (1986) |
| Interleukin-4 (IL-4) | Yakota et al., Proc. Natl. Acad. Sci., USA 83:5894–5898 (1986) |
| Interleukin-5 (IL-5) | Harada et al., J. Immunol. 134:3944–3951 (1985) |
| Interleukin-6 (IL-6) | Hirano et al., Nature 324:73–76 (1986) |
| Interleukin-7 (IL-7) | Goodwin et al., Proc. Natl. Acad. Sci., USA 86:302–306 (1989) |
| Interleukin-8 (IL-8) | Schmid and Weissmann, J. Immunol. 139:250–256 (1987) |
| Interleukin-9 (IL-9) | Yang et al., Blood 74:1880-11-884 (1989) |
| Interleukin-10 (IL-10) | Vieira et al., Proc. Natl. Acad. Sci., USA 88:1172–1176 (1991) |
| Interleukin-11 (IL-11) | Paul et al., Proc. Natl. Acad. Sci., USA 87:7512–7516 (1990) |
| Interleukin-12 (IL-12) | Wolf et al., J. Immunol. 146:3074–3081 (1991) |
| Interleukin-13 (IL-13) | Cherwinski et al., J. Exp. Med. 166:1229–1244 (1987) Brown et al., J. Immunol. 142:679–687 (1989) |
| Interleukin-14 (IL-14) | Ambrus et al., Proc. Natl. Acad. Sci., USA 90:6330–6334 (1993) |
| Interleukin-15 (IL-15) | Grabstein et al., Science 264:965–968 (1994) |
| Interleukin-16 (IL-16) | Baier et al., Proc. Natl. Acad. Sci., USA 94:5273–5279 (1997) |
| Interferon-α (IFN-α) | Pestka et al., Annu. Rev. Biochem. 56:727–777 (1987) |
| Interferon-β (IFN-β) | Pestka et al., supra, 1987 |
| Interferon-γ (IFN-γ) | Vilcek et al., Lymphokines 11:1–32 (1985) |
| Leukemia-inhibitory factor (LIF) | Gearing et al., Annals NY Acad. Sci. 628918 (1991) |
| Oncostatin M (OSM) | Malik et al., Mol. Cell. Biol. 9:2847–2853 (1989) |
| Transforming growth factor β (TGF-β) | Sporn and Roberts (Eds), Handbook of Experimental Phar. Springer-Verlag Vol 65: 419–472 |
| Tumor necrosis factor-α (TNF-α) | Wang et al., Science 228:149–154 (1985) |
| Tumor necrosis factor-β (TNF-β) | Gray et al., Nature 312:721–724 (1984) |
| Dendritic cell chemokine 1 (DC-CK1) | Adema et al., Nature 387:713–717 (1997) |
| Granulocyte-Macrophage Colony Stimulating Factor (GM-CSF) | Lee et al., Proc. Natl. Acad. Sci., USA 82:4360–4364 (1985) |
| Colony Stimulating Factor 1 (CSF-1) | Kawasaki et al., Science 230:291–296 (1985) |
| Granulocyte Colony Stimulating Factor (GCSF) | Negata et al., Nature 319:415–418 (1986) |
| Macrophage chemotactic and activating factor (MCAF) | Furutani et al., Biochem. Biophys. Res. Comm. 159:249–255 (1989) |
| Macrophage inflammatory protein-1 (MIP-1) | Zipfel et al., J. Immunol. 142:1582–1590 (1989) Blum et al., DNA Cell. Biol. 9:589–602 (1990) |
| Macrophage inflammatory protein-1 (MIP-1) | Lipes et al., Proc. Natl. Acad. Sci., USA 85:9704–9708 (1988); Brown et al., J. Immunol. 142:679–687 (1989) |
| RANTES | Schall et al., J. Immunol. 141:1018–1025 (1988) |
| Neutrophil-activating protein (NAP-2) | Walz et al., J. Exp. Med. 170:1745–1750 (1989) |
| Platelet factor 4 (PF-4) | Poncz et al., Blood 69:219–223 (1987) |

An immunomodulatory molecule can have the sequence of a naturally occurring immunomodulatory molecule or can have an amino acid sequence with substantial amino acid sequence similarity to the sequence of a naturally occurring immunomodulatory molecule. Thus, it is understood that limited modifications to a naturally occurring sequence can be made without destroying the biological function of an immunomodulatory molecule. For example, minor modifications of GM-CSF that do not destroy polypeptide activity fall within the definition of GM-CSF. These modifications can be deliberate, as through site-directed mutagenesis, or can be accidental such as through mutation in hosts harboring an encoding nucleic acid. All such modified polypeptides are included in the definition of an immunomodulatory molecule as at least one biological function of the immunomodulatory molecule is retained.

A cytokine antagonist also can be an immunomodulatory molecule useful in the invention. Such cytokine antagonists can be naturally occurring or non-naturally occurring and include, for example, antagonists of GM-CSF, G-CSF, IFN-γ, IFN-α, TNF-α, TNF-β, IL-1, IL-2, IL-3, IL-4, IL-6, IL-7, IL-10, IL-12, lymphotactin and DC-CK1. Cytokine antagonists include cytokine deletion and point mutants, cytokine derived peptides, and soluble, dominant negative portions of cytokine receptors. Naturally occurring antagonists of IL-1, for example, can be used in a vaccine of the invention to inhibit the pathophysiological activities of IL-1. Such IL-1 antagonists include IL-1Ra, which is a polypeptide that binds to IL-1 receptor I with an affinity roughly equivalent to that of IL-1α or IL-1β but that does not activate the receptor (Fischer et al., *Am. J. Physiol.* 261:R442–R449 (1991); Dinarello and Thomson, *Immunol. Today* 12:404–410 (1991), each of which are incorporated herein by reference). IL-1 antagonists also include IL-1β derived peptides and IL-1 muteins (Palaszynski et al., *Biochem. Biophys. Res. Commun.* 147:204–209 (1987), which is incorporated herein by reference). Cytokine antagonists useful in the invention also include, for example, antagonists of TNF-α (Ashkenazi et al., *Proc. Natl. Acad. Sci., USA* 88:10535–10539 (1991); Mire-Sluis, *Trends in Biotech.* 11:74–77 (1993), each of which are incorporated herein by reference).

Heat shock proteins (HSPs) also are immunomodulatory molecules useful in the vaccines and methods of the invention. Heat shock proteins, which are induced by stress-causing conditions such as heat shock or glucose deprivation, can produce a generalized anti-inflammatory response, thereby aiding in elimination of, for example, tumor cells or infected cells. Heat shock proteins are distinguished by their molecular mass and grouped in families and include HSP110, HSP90, HSP70, HSP60, HSP25, HSP20 and HSP8.5. Several heat shock proteins, including HSP60, HSP70 and HSP90, are expressed on the cell surface of mycobacteria-infected, HIV-infected cells or tumor cells (Multhoff et al, *Int. J. Cancer* 61:1–8 (1995), which is incorporated herein by reference). The mycobacterial heat shock protein HSP65 (Silva et al., *Infect. Immun.* 64:2400–2407 (1996), which is incorporated herein by reference) is an example of an immunomodulatory molecule useful in the vaccines of the invention.

The term "membrane attachment domain," as used herein, refers to a domain that spans the width of a cell membrane, or any part thereof, and that functions to attach a polypeptide to a cell membrane. Membrane attachment domains useful in the vaccines of the invention are those domains that function to attach a polypeptide to a cell surface membrane, such as the plasma membrane of an eukaryotic cell or the outer membrane of a prokaryotic cell. One skilled in the art understands that an appropriate membrane attachment domain is selected based on the type of cell in which the membrane-bound fusion protein is to be expressed.

A variety of naturally occurring and synthetic membrane attachment domains derived from eukaryotic and prokaryotic cell surface proteins are useful in the vaccines of the invention. For use in higher eukaryotic cells such as mammalian cells, a membrane attachment domain can be, for example, the membrane-spanning region of an integral membrane protein such as a cell surface receptor or cell adhesion molecule. Membrane attachment domains useful in the invention can be derived, for example, from cell surface receptors including growth factor receptors such as platelet derived growth factor receptor, epidermal growth factor receptor or fibroblast growth factor receptor; hormone receptors; cytokine receptors and T cell receptor. Membrane attachment domains useful in the invention also can be derived from cell adhesion molecules such as cadherins, integrins, selectins and members of the immunoglobulin superfamily; as well as other integral membrane proteins such as CD antigens. The amino acid sequences of exemplary membrane attachment domains are provided in Table 2 (see, also Pigott and Power, *The adhesion Molecule Facts Book* San Diego: Academic Press, Inc. (1993) and Barclay et al., *The Leukocyte Antigen Facts Book* San Diego: Academic Press, Inc. (1993), each of which is incorporated herein by reference). If desired, the fusion protein can include the cytosolic domain, or portion thereof, of the heterologous protein from which the membrane attachment domain is derived.

Type I membrane attachment domains are transmembrane sequences of about 25 hydrophobic amino acid residues usually followed by a cluster of basic amino acids. Amino acids that are usually excluded from such membrane attachment domains include Asn, Asp, Glu, Gln, His, Lys and Arg, although where the domains form a multimeric complex in the membrane, there can be charged residues present. The orientation of a type I membrane attachment domain is such that the amino-terminal portion is extracellular. Such type I membrane attachment domains can be derived, for example, from CD2, CD40 or the IL-4 receptor.

Type II membrane attachment domains are transmembrane domains useful in the vaccines of the invention. The orientation of a type II membrane attachment domain is such that the carboxy-terminal portion is extracellular. Examples of type II membrane attachment domains include the transmembrane domain of CD72.

A membrane attachment domain of the invention also can be a phosphatidylinositol-glycan (PI-G) anchor, which is attached to the carboxy-terminal residue of a protein. A PI-G anchor can be derived, for example, from human placental alkaline phosphatase (HPAP), and can function to anchor a fusion protein to the cell surface (see, for example, Whitehorn et al., *Biotechnology* 13:1215–1219 (1995), which is incorporated herein by reference). PI-G-anchored molecules have a signal sequence at their carboxy-terminus that is cleaved off and replaced by the PI-G anchor. The residues at the PI-G attachment site and immediately following are typically small amino acids such as Ala, Asn, Asp, Gly, Cys or Ser. After the attachment residue, there is a hydrophobic sequence of about 10 to 20 residues starting 7–10 residues after the attachment point. Such hydrophobic PI-G-signal sequences generally lack the basic charged residues found in type I membrane attachment domains.

Type III membrane attachment domains, or segments thereof, also can be useful in the vaccines of the invention. Such type III membrane attachment domains are derived from eukaryotic cell surface molecules that cross the lipid bilayer numerous times. A membrane attachment domain useful in the invention can be, for example, one or more transmembrane domains derived from MDR1, a G-protein linked receptor or a protein of the rhodopsin superfamily.

TABLE 2

Exemplary Membrane Attachment Domains

| Source | SIN: | Sequence of membrane attachment domain |
|---|---|---|
| P-Cadherin | 4 | FILPILGAVLALLLLLTLLALLLLV |
| CD2 | 5 | IYLIIGICGGGSLLMVFVALLVFYIT |
| CD40 | 6 | ALVVIPIIFGILFAILLVLVFI |
| Contactin | 7 | ISGATAGVPTLLLGLVLPAP |
| IL-4 receptor | 8 | LLLGVSVSCIVILAVCLLCYVSIT |
| Mannose receptor | 9 | VAGVVIIVILLILTGAGLAAYFFY |
| M-CSF receptor | 10 | FLFTPVVVACMSIMALLLLLLLLL |
| PDGFR β chain | 11 | VVVISAILALVVLTIISLIILIMLWQK KPR |
| PDGFR α chain | 12 | ELTVAAAVLVLLVIVSISLIVLVVTW |
| P-Selectin | 13 | LTYFGGAVASTIGLIMGGTLLALL |
| Rat Thy-1 | 14 | VKCGGISLLVQNTSWLLLLLLSLSFLQ ATDFISL |
| TNFR-1 | 15 | TVLLPLVIFFGLCLLSLLFIGLM |
| VCAM-1 | 16 | LLVLYFASSLIIPAIGMIIYFAR |

A membrane attachment domain useful in a bacterial vaccine of the invention can be derived, for example, from outer membrane protein A (OmpA). For example, a transmembrane domain containing amino acids 46 to 159 of OmpA, which encodes five of the eight membrane-spanning segments of the native protein, can be a membrane attachment domain particularly useful in the invention (Francisco et al., *Proc. Natl. Acad. Sci., USA* 89:2713–2717 (1992); Francisco et al., *Biotechnol.* 11:491–495 (1993); Francisco et al., *Proc. Natl. Acad. Sci., USA* 90:10444–10448 (1993); Francisco and Georgiou, *Annals New York Acad. Sci.* 745:372–382 (1994), each of which are incorporated herein by reference).

The term "heterologous," as used herein in reference to a membrane attachment domain operatively fused to a non-antibody immunomodulatory molecule, means a membrane attachment domain derived from a source other than the gene encoding the non-antibody immunomodulatory molecule. A heterologous membrane attachment domain can be synthetic or can be encoded by a gene distinct from the gene encoding the non-antibody immunomodulatory molecule to which it is fused.

The term "operatively fused," as used herein in reference to a non-antibody immunomodulatory molecule and a heterologous membrane attachment domain, means that the immunomodulatory molecule and membrane attachment domain are fused in the correct reading frame such that, under appropriate conditions, a full-length fusion protein is expressed. One skilled in the art would recognize that such a fusion protein can comprise, for example, an amino-terminal immunomodulatory molecule operatively fused to a carboxyl-terminal heterologous membrane attachment domain or can comprise an amino-terminal heterologous membrane attachment domain operatively fused to a carboxyl-terminal immunomodulatory molecule.

The term "membrane-bound," as used herein in reference to a fusion protein of the invention, means stably attached to a cellular membrane. In a vaccine of he invention, a membrane-bound fusion protein of the invention is expressed on the surface of a cell.

The term "fusion protein," as used herein, means a hybrid protein including a synthetic or heterologous amino acid sequence. A fusion protein can be produced, for example, from a hybrid gene containing operatively linking heterologous gene sequences.

The term "cell," as used herein in reference to a vaccine of the invention, means any prokaryotic or eukaryotic cell capable of having expressed on its cell surface a membrane-bound fusion protein. The term cell includes live, attenuated and killed cells and encompasses primary cells, normal cells, immortalized cells, transformed cells, tumor cells or infected cells. In the methods of the invention, a cell can be autologous, allogeneic or xenogeneic to the individual to whom the vaccine is administered. Cells useful in the vaccines of the invention include mammalian cells and, in particular, human cells of a variety of cell types. In addition, the cellular vaccines of the invention can be made from bacterial cells such as *Escherichia coli*, Salmonella, *Listeria monocytogenes* and *Mycobacterium bovis*.

Tumor cells to be genetically modified can be obtained, for example, by biopsy from a subject having cancer, and the tumor cells subsequently modified to contain a membrane-bound fusion protein including a non-antibody immuno-modulatory molecule operatively fused to a heterologous transmembrane domain. Alternatively, donor tumor cells or cells from a tumor cell line can be genetically modified to produce a vaccine of the invention.

A variety of tumor cells, especially human tumor cells such as melanoma cells, colon tumor cells, breast tumor cells, prostate tumor cells, glioblastoma cells, renal carcinoma cells, neuroblastoma cells, lung cancer cells, bladder carcinoma cells, plasmacytoma or lymphoma cells, for example, can be genetically engineered to express a membrane-bound fusion protein including a non-antibody immunomodulatory molecule operatively fused to a heterologous membrane attachment domain. In a vaccine to protect against or treat melanoma, human melanoma cell lines such as the M12, M24, M101 and SK-MEL cell lines can be useful in preparing a vaccine of the invention (Chi et al., *Amer. J. Pathol.* 150:2143–2152 (1997), which is incorporated herein by reference).

The vaccines of the invention also can be used to protect against or treat colon cancer. Colon tumor cells can be obtained from culturing resected tumors or from established human colon tumor cells lines such as HCT 116, Colo205, SW403 or SW620. Such cells are available to one skilled in the art, for example, from the American Type Culture Collection (ATCC; Rockville, Md.).

The vaccines of the invention also can be used to protect against or treat breast cancer. Primary breast tumor cells cultured from surgically resected tumors or human breast tumor cell lines such as the BT-20 line also can be useful preparing vaccines for protection against and treatment of breast cancer.

A vaccine of the invention also can be used to protect against or treat prostate cancer, which is the second most frequent tumor of males in the United States. Prostate cells for used in such vaccines can be primary prostate cells obtained from surgically resected tumors or can be a prostate tumor cell line such as the LNCaP line (see Horoszewicz et al., *Cancer Res.* 43:1809 (1983), which is incorporated herein by reference).

For protection against or treatment of brain tumors, one can prepare a vaccine of the invention using primary human glioma cells or cells from established human glioblastoma or astrocytoma lines. Primary cultures of glioma cells can be established from surgically resected tumor tissue as described in Wakimoto et al., *Japan. J. Cancer Res.* 88:296–305 (1997), which is incorporated herein by reference. Human glioblastoma cell lines, such as U-87 MG or U-118 MG, or human astrocytoma lines, such as CCF-STTG1 or SW1088 (Chi et al., supra, 1997), can be obtained from ATCC. Any of such cells can be used to produce a vaccine that contains an immunomodulatory molecule such as GM-CSF, IL-2, IL-4, IL-6, IL-7, TNF-α or IFN-γ for protection against or treatment of human brain tumors.

It is recognized that the tumor cells to be administered can be viable. However, one skilled in the art understands that administration of a viable tumor cell vaccine to a subject requires that the tumor cells be inactivated so they do not grow in the subject. Inactivation can be accomplished by any of various methods, including, for example, by irradiation, which is administered to the cells at a dose that inhibits the ability of the cells to replicate but does not initially kill the tumor cells (see Example II). Such viable tumor cells can express a membrane-bound fusion protein but cannot proliferate to form new tumors.

Non-transformed cells including fibroblasts, myoblasts, leukocytes, hepatocytes, endothelial cells and dendritic cells, and especially non-transformed human cells, also are useful in the vaccines of the invention. In particular, where a disease-associated antigen or immunogenic epitope has been isolated, a fibroblast-based vaccine of the invention can be engineered to include the disease-associated antigen or immunogenic epitope of interest. Such disease-associated antigens and immunogenic epitopes thereof, including tumor-associated antigens and autoimmune disease-associated antigens, are described further below. Fibroblasts useful in the invention include autologous fibroblasts obtained from the individual to be vaccinated. Such primary human fibroblasts are readily obtained, for example, by punch biopsy of the skin, or from tissues such as lung, liver or bone marrow. Fibroblasts useful in the invention also can be primary fibroblasts such as HFL-1 cells; the MRC-9 fibroblast cell line; and immortalized fibroblast cell lines including those immortalized with 4-nitroquinoline 1-oxide or $^{60}CO$ gamma rays such as the KMST-6, SUSM-1, and OUMS-24F lines (Iijima et al., *Int. J. Cancer* 66:698–702 (1996), which is incorporated herein by reference). Fibroblasts are particularly useful in the vaccines of the invention since fibroblasts are readily cultured and propagated in vitro (Treco et al., "Fibroblast Cell Biology and Gene Therapy," in Chang (Ed.), *Somatic Gene Therapy* CRC Press, Boca Raton (1995), which is incorporated herein by reference).

A panel of vaccines produced from multiple donor cells or cell lines can represent a variety of diseased cells and can express or have expressed a variety of different disease-associated antigens. For example, a panel of anti-tumor vaccines produced from multiple donor tumor cells, tumor cell lines or transfected non-tumor cell lines can represent various histologic tumor types and express various known tumor antigens such as MZ2-E or mucin (see Finn, supra, 1993). Such a panel of anti-tumor vaccines, for example, can be maintained in a cell repository in a form readily available for administration to an individual predisposed to developing a particular tumor type. The skilled artisan can select an appropriate genetically modified donor tumor cell from the panel based, for example, on the histologic type of tumor the individual has or is predisposed to developing.

Bacterial cells also are useful in the cellular vaccines of the invention. Live bacterial vaccines using, for example, attenuated strains of bacteria are particularly useful since such live vaccines generally can confer a stronger, longer-lasting immune response than killed vaccines. Live bacterial vaccines can establish limited infections in the host that mimic the early stages of natural infection and lead to a natural immune response, and can confer extended immunity since the bacteria remain viable in the host for a long time. In addition, bacterial outer membrane proteins, lipopolysaccharides (LPS) and secreted bacterial toxins are strongly immunogenic and can act as natural adjuvants to enhance an immune response against a recombinant antigen. Furthermore, such live bacterial vaccines are easily administered, for example, orally (Francisco and Georgiou, supra, 1994).

A variety of avirulent bacterial strains have been developed for use as live vaccines. Bacteria useful in the cellular vaccines of the invention include Salmonellae, *Vibrio cholerae, Mycobacterium bovis, Streptococcus gordonii, Escherichia coli*, shigella, lactobacillus, *Listeria monocytogenes* and *Bacillus subtilis* (see, for example, Curtiss, "Attenuated Salmonella Strains as Live Vectors for the Expression of Foreign Antigens," in Woodrow and Levine (Ed.), *New Generation Vaccines* Marcel Dekker, Inc. (1990); Cardenas and Clements, *Clin. Microbiol. Rev.* 5:328–342 (1992); Cirillo et al., *Clin. Infect. Dis.* 20:1001–1009 (1995); and Fortaine et al., *Res. Microbiol.* 141:907–912 (1990), each of which is incorporated herein by reference). Bacteria useful in the vaccines of the invention also include *Shigella flexneri, Yersinia enterocolitica, bordetella pertussis* and *Staphylococcus xylosus* (Ryd et al., *Microbial. Pathogen.* 12:399–407 (1992); van Damme et al., *Gastroenterol.* 103:520–531 (1992); and Renauld-Mongenie et al., *Proc. Natl. Acad. Sci., USA* 93:7944–7949 (1996), each of which is incorporated herein by reference). Yeast cells such as Saccharomyces cerevisiae also can be useful in the vaccines of the invention, particularly in expressing membrane-bound fusion proteins that require post-translational modifications for activity.

Salmonella cells are particularly useful in the vaccines of the invention. Salmonella strains with mutations in genes such as aroA, aroC, aroD, cya, crp, gale, and phoP/phoQ are unable to sustain proliferation within mammalian cells. However, such live attenuated strains grow intracellularly long enough to stimulate an immune response. Attenuated Salmonella strains include nutritional auxotrophs such as those that are defective in biosynthesis of aromatic metabolites and that render the organism auxotrophic for PABA and 2,3-dihydroxybenzoate. These attenuated strains have mutations in the aro genes, for example, deletions in one or more of the aroA, aroC or aroD genes. Deletions in adenylate cyclase (cya) and cyclic 3',5'-AMP receptor protein (crp) genes also are useful in generating attenuated Salmonella strains. Live attenuated Salmonella vaccines can be prepared using, for example, *S. typhimurium* strains such as ΔaroA ΔaroD BRD509, ISP1820ΔaroC ΔaroD, Ty2ΔaroC ΔaroD and Ty2Δcya Δcrp (see, for example, Tacket et al., *Infect. Immun.* 60:536–541 (1992); Turner et al., *Infect. Immun.* 61:5374–5380 (1993); Dunstan et al., *Infect. Immun.* 64:2730–2736 (1996); Londoho et al., *Vaccine* 14:545–552 (1996), each of which are incorporated herein by reference). Expression vectors for use in Salmonella include pKK233-2 and are well known in the art (Amann and Brosius, *Gene* 40:183–190 (1985); see, also, Anderson et al., "Development of Attenuated Salmonella Strains that Express Heterologous Antigens" in Robinson et al., *Methods in Molecular Medicine: Vaccine Protocols* Humana Press, Inc. Totowa, N.J., each of which are incorporated herein by reference).

*Listeria monocytogenes* also are bacteria useful in the vaccines of the invention. *L. monocytogenes* based vaccines are useful, for example, to stimulate an immune response against influenza virus infection (Ikonomidis et al., *Vaccine* 15:433–440 (1997), which is incorporated herein by reference). Furthermore, *L. monocytogenes* can be engineered to express a disease-associated antigen or immunogenic epitope thereof, such as a tumor-associated antigen, for stimulation of an immune response to protect against or treat cancer (see, for example, Paterson and Ikonomidis, *Curr. Opin. Immunol.* 8:664–669 (1996), which is incorporated herein by reference).

An attenuated strain of *Mycobacterium bovis*, Bacillus Calmette-Guerin (BCG), also can be useful in the vaccines of the invention (Irvine and Restifo, *Seminars in Cancer Biology* 6:337–347 (1995); Stover et al, *Nature* 351:456–460 (1991), each of which is incorporated herein by reference). BCG has been administered successfully as a tuberculosis vaccine, and components of the cell wall of BCG have powerful adjuvant activity. Mycobacterial expression vectors, which are useful for expressing a membrane-bound fusion protein and, if desired, a disease-associated antigen or immunogenic epitope thereof in a vaccine of the invention, are well known in art (Jacobs et al., *Nature* 327:532–535 (1987) and Snapper et al., *Proc. Natl. Acad. Sci., USA* 85:6987–6991 (1988), each of which are incorporated herein by reference). One skilled in the art understands that these and other eukaryotic and prokaryotic host cells can be used in the vaccines and methods of the invention.

Expression vectors useful in the cellular vaccines of the invention include prokaryotic and eukaryotic expression vectors. Such expression vectors, including plasmids, cosmids, and viral vectors such as bacteriophage, baculovirus, retrovirus and DNA virus vectors, are well known in the art (see, for example, *Meth. Enzymol.*, Vol. 185, D. V. Goeddel, ed. (Academic Press, Inc., 1990) and Kaplitt and Loewy (Ed.), *Viral Vectors: Gene Therapy and Neuroscience Applications* (Academic Press, Inc., 1995), each of which are incorporated herein by reference). Expression vectors contain the elements necessary to achieve constitutive or inducible transcription of a nucleic acid molecule encoding a membrane-bound fusion protein. Eukaryotic expression vectors that result in high levels of sustained expression, such as vectors including cytomegalovirus (CMV), rous sarcoma virus (RSV), or simian virus 40 (SV40) promoter/enhancer elements, are particularly useful in the vaccines of the invention. Commercially available expression plasmids with strong promoter/enhancer elements include pHOOK™-1, pHOOK™-2, pHOOK™-3, pcDNA3.1, pcDNA3.1/Hygro and pcDNA3.1/Zeo from Invitrogen (Carlsbad, Calif.). The pHOOK™-1, pHOOK™-2 and pHOOK™-3 expression plasmids include a nucleotide sequence encoding the human platelet derived growth factor β receptor membrane attachment domain and, thus, are particularly useful in the vaccines of the invention (see Example I). One of ordinary skill in the art would know which procaryotic or eukaryotic host systems are compatible with a particular vector.

An expression vector encoding a membrane-bound fusion protein can be introduced into a cell to produce a vaccine of the invention by any of a variety of methods known in the art and described, for example, in Sambrook et al., *Molecular Cloning: A Laboratory Manual*, 2nd Ed, Vols 1 to 3, Cold Spring Harbor Laboratory Press, New York (1989), and in Ausubel et al., *Current Protocols in Molecular Biology*, John Wiley and Sons, Baltimore, Md. (1994), each of which are incorporated herein by reference. Such methods include, for example, transfection via lipofection or electroporation to introduce recombinant expression vectors into eukaryotic cells. The introduction of the pHOOK™.1 expression vector into CT-26 cells is described in Example I.

In one embodiment, the cellular vaccine further includes a disease-associated antigen or immunogenic epitope thereof. Disease-associated antigens can be endogenous or exogenous to the cell and include tumor-associated antigens, autoimmune disease-associated antigens, infectious disease-associated antigens, viral antigens, parasitic antigens and bacterial antigens.

The term "disease-associated antigen," as used herein, means a molecule present on the surface of a diseased cell that can induce a cell-mediated or humoral immune response. Disease-associated antigens can be selectively expressed on particular disease cells, or can be expressed on both diseased and normal cells.

The term "immunogenic epitope thereof," as used herein in reference to a disease-associated antigen, means a portion of an antigen that functions as an antigenic determinant to induce a cell-mediated or humoral immune response against the disease-associated antigen. Both T cell and B cell epitopes are encompassed within the term immunogenic epitope.

As used herein in reference to a disease-associated antigen and a cell, the term "endogenous" means a disease-associated antigen originating within the cell.

As used herein in reference to a disease-associated antigen and a cell, the term "exogenous" means a disease-associated antigen originating within the cell. Exogenous disease-associated antigens can be conveniently expressed in a cell having a membrane-bound fusion protein using recombinant methods well known in the art.

A variety of tumor-associated antigens are useful in the vaccines and methods of the invention (see Table 3). Such tumor-associated antigens include those which are tumor-specific as well as those which are tumor-selective. Tumor-associated antigens include p53 and mutants thereof, Ras and mutants thereof, Bcr/Abl breakpoint peptides, HER-2/Neu, HPV E6, HPV E7, carcinoembryonic antigen, MUC-1, MAGE-1, MAGE-3, BAGE, GAGE-1, GAGE-2, N-acetylglucosaminyltransferase-V, p15, gp100, MART-1/MelanA, tyrosinase, TRP-1, β-catenin, MUM-1 and CDK-4.

A tumor-associated antigen can be an oncogenic protein such as a nonmutated, overexpressed oncoprotein or a mutated, unique oncoprotein (Disis and Cheever, *Current Opin. Immunol.* 8:637–642 (1996); Cornelis et al., *Curr. Opin. Immunol.* 8:651–657 (1996, each of which are incorporated herein by reference). For example, mutations in p53 are present in about 50% of human malignancies, and a mutant p53 protein or peptide fragment thereof can be a tumor-associated antigen useful in the invention (Yanuck et al., *Cancer Res.* 53:3257–3261 (1993); Noguchi et al., *Proc.* *Natl. Acad. Sci, USA* 92:2219–2223 (1995), each of which are incorporated herein by reference). A tumor-associated antigen useful in a vaccine of the invention also can be a normal p53 protein or peptide fragment thereof (Theobald et al., *Proc. Natl. Acad. Sci., USA* 92:11993–11997 (1995); Houbiers et al., *Immunol.* 23:2072–2077 (1993), each of which are incorporated herein by reference). Although p53 is present in both normal and tumor cells, vaccines including normal p53 peptides can promote a selective immune response against tumor cells due to the relative increased accumulation of p53 in the cytosol of tumor cells.

Mutations in Ras are present in about 15% of human malignancies. Mutant Ras proteins and peptides fragments thereof can be tumor-associated antigens useful in vaccines for treating such malignancies. Mutant Ras proteins usually have a single amino acid substitution at residue 12 or 61; Ras peptides spanning this mutant segment can be useful tumor-associated antigens (Cheever et al., *Immunol. Rev.* 145:33–59 (1995); Gjertsen et al., *Lancet* 346:1399–1400 (1995); Abrams et al., *Seminars Oncol.* 23:118–134 (1996); Abrams et al., *Eur. J. Immunol.* 26:435–443 (1996), each of which are incorporated herein by reference).

HER-2/neu also is a tumor-associated antigen, and peptides derived from the HER-2/neu proto-oncogene can be useful in the vaccines and methods of the invention (Disis et al., *Cancer Res.* 54:1071–1076 (1994); Bernhard et al., *Cancer Res.* 55:1099–1104 (1995); Mayordomo et al., *Nature Med.* 1:1297–1302 (1995), each of which is incorporated by reference herein). HER-2/neu is a growth factor receptor overexpressed in 30% of breast and ovarian cancers and in a wide variety of other adenocarcinomas.

A tumor-associated antigen useful in the vaccines of the invention also can be the epidermal growth factor receptor (EGFR) or immunogenic epitope thereof, or a mutant EGFR variant or immunogenic epitope thereof. For example, the EGFR deletion mutant EGFRvIII is expressed in a subset of breast carcinomas and in non-small cell lung carcinomas and malignant gliomas. EGFRvIII disease-associated antigens, such as peptides corresponding to the novel EGFRvIII fusion junction, can be useful in stimulating an immune response against such tumors (Wikstrand et al., *Cancer Res.* 55:3140–3148 (1995); Moscatello et al., *Cancer Res.* 57:1419–1424 (1997), each of which are incorporated herein by reference). Thus, EGFR or EGFRvIII disease-associated antigens or immunogenic epitopes thereof can be useful in vaccines for the treatment of breast and lung carcinomas and malignant gliomas and to protect individuals at high risk from developing these cancers.

A tumor-associated antigen also can be a joining region segment of a chimeric oncoprotein such as Bcr-Abl (Ten-Bosch et al., *Leukemia* 9:1344–1348 (1995); Ten-Bosch et al., *Blood* 87:3587–3592 (1996), each of which are incorporated herein by reference).

A tumor-associated antigen useful in the vaccines of the invention also can be an E6 or E7 viral oncogene such as a human papilloma virus (HPV) E6 or E7 viral oncogene or immunogenic epitope thereof. For example, HPV16 is one of the major human papillomavirus types associated with cervical cancer, and immunogenic peptide epitopes encoded by HPV16 E6 and E7 can be useful in vaccines for the prevention and treatment of cervical carcinoma (see Ressing et al., *J. Immunol.* 154:5934–5943 (1995); Ressing et al., *Cancer Res.* 56:582–588 (1996), each of which are incorporated herein by reference).

A tumor-associated antigen useful in the vaccines of the invention also can be carcinoembryonic antigen (CEA). This antigen is highly expressed in the majority of colorectal, gastric and pancreatic carcinomas (Tsang et al., *J. Natl. Cancer Inst.* 87:982–990 (1995), which is incorporated herein by reference).

The MUC-1 mucin gene product, which is an integral membrane glycoprotein present on epithelial cells, also is a tumor-associated antigen useful in the invention. Mucin is expressed on almost all human epithelial cell adenocarcinomas, including breast, ovarian, pancreatic, lung, urinary bladder, prostate and endometrial carcinomas, presenting more than half of all human tumors (see, for example, Fin et al., *Immunol. Rev.* 145:61–89 (1995); Barratt-Boyes, *Cancer Immunol. Immunother.* 43:142–151 (1996), which are incorporated herein by reference). Vaccines of the invention containing full-length mucin or immunogenic epitopes thereof can therefore be used to protect against or treat epithelial cell adenocarcinomas such as breast carcinomas (Lalani et al., *J. Biol. Chem.* 266:15420–15426 (1991), which is incorporated herein by reference)

Minor histocompatibility antigens also can be used as tumor-associated antigens in the vaccines of the invention (Goulmy, *Curr. Opin. Immunol.* 8:75–81 (1996); Den Haan et al., *Science* 268:1478–1480 (1995); Wang et al., *Science* 269:1588–1590 (1995), each of which are incorporated herein by reference). For example, an HLA-A2 antigen can be used in the vaccines of the invention to treat human renal cell carcinomas (Brandle et al., *J. Exp. Med.* 183:2501–2508 (1996), which is incorporated herein by reference).

A variety of widely shared melanoma antigens also can be tumor-associated antigens useful in the vaccines of the invention (Robbins and Kawakami, *Curr. Opin. Immunol.* 8:628–636 (1996); Celli and Cole, *Seminars Oncol.* 23:754–758 (1996), each of which are incorporated herein by reference). For example, the MAGE-1, MAGE-2, MAGE-3, BAGE, GAGE-1 and GAGE-2 tumor-associated antigens or immunogenic epitopes thereof such as MZ2-E can be used in the vaccines of the invention for protection against and treatment of melanoma (van der Bruggen, *Science* 254:1643–1647 (1991), which is incorporated herein by reference). In normal adult tissue, the expression of MAGE related gene products is limited to testes and placenta; however, these tumor-associated antigens are expressed in a wide variety of tumor types, including breast carcinomas and sarcomas. A widely expressed melanoma tumor-associated antigen useful in the vaccines of the invention also can be, for example, N-acetylglucosaminyltransferase-V, which is expressed at significant levels in about 50% of melanomas and absent in normal tissues (Guilloux et al., *J. Exp. Med.* 183:1173–1183 (1996), which is incorporated herein by reference).

Melanoma tumor-associated antigens also can be differentiation antigens expressed by normal melanocytes. Such melanoma tumor-associated antigens include MART-1/MelanA; gp100; tyrosinase, the key enzyme in pigment synthesis; and the tyrosinase-related protein TRP-1 (gp75).

Unique melanoma antigens also can be tumor-associated antigens useful in the vaccines of the invention (Mumberg et al., *Seminars in Immunol.* 8:289–293 (1996), which is incorporated herein by reference). Such unique tumor-associated antigens include the MUM-1, β-catenin, and cyclin-dependent kinase CDK4 melanoma

TABLE 3

EXEMPLARY DISEASE-ASSOCIATED ANTIGENS

| Antigen | Epitope | Reference |
|---|---|---|
| Non-melanoma antigens | | |
| HER-2/neu | IISAVVGIL (17)* | Peoples et al., Proc. Natl. Acad. Sci. USA. 92: 432–436 (1995) |

TABLE 3-continued

EXEMPLARY DISEASE-ASSOCIATED ANTIGENS

| Antigen | Epitope | Reference |
|---|---|---|
| | KIFGSLAFL (18) | Fisk et al., J. Exp. Med. 181: 2109–2117 (1995) |
| HPV E6, HPV E7 | YMLDLQPETT (19) | Ressing et al., Cancer Res. 56: 582–588 (1996) |
| MUC-1 | PDTRPAPGSTAPPAHGV TSA (20) | Fin et al., Immunol Rev. 145: 61–89 (1995) |
| Tumor-specific, widely shared antigens | | |
| MAGE-1 | EADPTGHSY (21) | Traversari et al., J. Exp. Med. 176: 1453–1457 (1992) |
| | SAYGEPRKL (22) | Van der Bruggen et al., Eur. J. Immunol. 24: 2134–2140 (1994) |
| MAGE-3 | EVDPIGHLY (23) | Gaugler et al., J. Exp. Med. 179: 91-21-930 (1994) |
| | FLWGPRALV (24) | Celis et al., Proc. Natl. Acad. Sci. USA. 91: 2105–2109 (1994) |
| BAGE | AARAVFLAL (25) | Boel et al., Immunity 2: 167–175 (1995) |
| GAGE-1, GAGE-2 | YRPRPRRY (26) | Van den Eynde et al., J. Exp. Med. 182: 689–698 (1995) |
| GnT-V | VLPDVFIRC (27) | Guilloux et al., J. Exp. Med. 183: 1173–1183 (1996) |
| p15 | AYGLDFYIL (28) | Robbins et al., J. Immunol 154: 5944–5950 (1995) |
| Melanocyte lineage proteins | | |
| gp100 | KTWGQYWQV (29) ITDQVPFSV (30) YLEPGPVTA (31) LLDGTATLRL (32) VLYRYGSFSV (33) | Kawakami et al., J. Immunol 154: 3961–3968 (1995) |
| MART-1/MelanA | AAGIGILTV (34) | Kawakami et al., J. Exp. Med. 180: 347–352 (1994) |
| | ILTVILGVL (35) | Castelli et al., J. Exp. Med. 181: 363–368 (1995) |
| TRP-1 (gp75) | MSLQRQFLR (36) | Wang et al., J. Exp. Med. 183: 1131–1140 (1996) |
| Tyrosinase | MLLAVLYCL (37) | Wölfel et al., Eur J. Immunol 24: 759–764 (1994) |
| | YMNGTMSQV (38) | Wölfel et al., supra, (1994) |
| | SEIWRDIDF (39) | Brichard et al., J. Immunol 26: 224–230 (1996) |
| | AFLPWHRLF (40) | Kang et al., J. Immunol 155: 1343–1348 (1995) |
| | QNILLSNAPLGPQ (41) SYLQDSDPDSFQD (42) | Topalian et al J. Exp. Med. 183: 1965–1971 (1996) |
| Tumor-specific antigens | | |
| β-catenin | SYLDSGIHF (43) | Robbins et al., J. Exp. Med. 183: 1185–1192 (1996) |
| MUM-1 | EEKLIVVLF (44) | Coulie et al., Proc. Natl. Acad. Sci. USA. 92: 7976–7980 (1995) |
| CDK4 | ACDPHSGHFV (45) | Wölfel et al., Science 269: 1281–1284 (1995) |

*SEQ ID NOS indicated in parenthesis antigens (Coulie et al., *Proc. Natl. Acad. Sci., USA* 92:7976–7980 (1995); Wolfel et al., *Science* 269:1281–1284 (1995); Robbins et al., *J. Exp. Med.* 183:1185–1192 (1996), each of which are incorporated herein by reference).

A disease-associated antigen of the invention can be a human immunodeficiency type I (HIV-1) antigen. Such antigens include the gp120 envelope glycoprotein and immunogenic epitopes thereof such as the principal neutralization determinant (PND); gp160; and HIV-1 core protein derived immunogenic epitopes (see Ellis (Ed.), *Vaccines: New Approaches to Immunological Problems* Stoneham, Mass.: Reed Publishing Inc. (1992), which is incorporated herein by reference).

The vaccines of the invention also can contain autoimmune disease-associated antigens and can be useful in protecting against or treating diseases such as rheumatoid arthritis, psoriasis, multiple sclerosis, systemic lupus erythematosus and Hashimoto's disease, type I diabetes mellitus, myasthenia gravis, Addison's disease, autoimmune gastritis, Graves' disease and vitiligo. Autoimmune disease-associated antigens can be, for example, T cell receptor derived peptides such as Vβ14, Vβ3, Vβ17, Vβ13 and Vβ6 derived peptides. Autoimmune disease-associated antigens also include annexins such as AX-1, AX-2, AX-3, AX-4, AX-4, AX-5 and AX-6, which are autoantigens associated with autoimmune diseases such as systemic lupus erythematosus, rheumatoid arthritis and inflammatory bowel disease (Bastian, *Cell. Mol. Life. Sci.* 53:554–556 (1997), which is incorporated herein by reference). In addition, the annexins can be tumor-associated antigens useful in the vaccines of the invention.

A variety of other disease-associated antigens also can be included in the vaccines of the invention. Such disease-associated antigens include viral, parasitic, yeast and bacterial antigens. For example, *Helicobacter pylori* is the major causative agent of superficial gastritis and plays a central role in the etiology of peptic ulcer disease. Infection with *H. pylori* also appears increase the risk of gastric cancer. The vaccines of the invention can be useful in protecting against *H. pylori* infection. Such vaccines can contain an *H. pylori* disease-associated antigen, for example, the urease protein, 90 kDa vacuolating cytotoxin (VacA), or 120 to 140 kDa immunodominant protein (CagA) of *H. pylori*, or immunogenic epitopes thereof (Clyne and Drumm, *Infect. Immun.* 64:2817 (1996); Ricci et al., *Infect. Immun.* 64:2829–2833 (1996), each of which are incorporated herein by reference).

The vaccines of the invention also can be used to prevent the chronic inflammatory condition of tooth-supporting tissue that results in adult periodontal disease. In particular, *Porphyormonas gingivalis* is recognized as an important etiological agent of such disease, and disease-associated antigens derived from *P. gingivalis* can be included in the vaccines of the invention for prevention and treatment of periodontal disease. *P. gingivalis* disease-associated antigens include the ArgI, ArgIA and ArgIB arginine-specific proteases of *P. gingivalis*, and immunogenic epitopes thereof including the GVSPKVCKDVTVEGSNEFAPVQNLT (SEQ ID NO:46) epitope (see, for example, Curtis et al., *Infect. Immun.* 64:2532–2539 (1996), which is incorporated herein by reference).

Additional disease-associated antigens useful in the vaccines of the invention include the MP65 antigen of *Candida albicans* (Gomez et al., *Infect. Immun.* 64:2577 (1996), which is incorporated herein by reference); helminth antigens; Mycobacterial antigens including *M. bovis* and *M. tuberculosis* antigens; Haemophilus antigens; Pertussis antigens; cholera antigens; malaria antigens; influenza virus antigens; respiratory syncytial viral antigens; hepatitis B antigens; poliovirus antigens; herpes simplex virus antigens; rotavirus antigens and flavivirus antigens (Ellis, supra, 1992).

In a further embodiment, the vaccine contains a disease-associated antigen or immunogenic epitope thereof operatively fused to the membrane-bound fusion protein. Such vaccines are particularly useful in expressing an exogenous disease-associated antigen and have the advantage that only a single expression vector is utilized for expression of the membrane-bound fusion protein containing the non-antibody immunomodulatory molecule and for expression of the disease-associated antigen or immunogenic epitope.

Soluble cytokine-antigen fusion proteins have previously been expressed, such as those containing an idiotypic antigen fused to GM-CSF, IL-2, IL-4, IFN-γ or an IL-1β peptide (Tao and Levy, *Nature* 362:755–758 (1993); Hakim et al., supra, 1996; Chen et al., *J. Immunol.* 153:4775 (1994), which is incorporated herein by reference). Such soluble cytokine-antigen fusion proteins elicited an anti-idiotype response that protected mice from tumor challenge and indicate that a variety of cytokines retain activity when expressed as fusion proteins.

In a vaccine of the invention, the membrane-bound fusion protein can contain an amino-terminal non-antibody immunomodulatory molecule operatively fused to a disease-associated antigen or immunogenic epitope thereof, which is operatively fused to a carboxyl-terminal heterologous membrane attachment domain. Membrane-bound fusion proteins including a disease-associated antigen or immunogenic epitope thereof can be readily produced by recombinant methods. For example, the GM-CSF/PDGFR membrane attachment domain construct described in Example I can be modified to include an operatively fused disease-associated antigen by cloning a nucleotide sequence encoding the antigen at the SalI site of pHOOK™-1.GM-CSF.

A vaccine of the invention also can include a second immunomodulatory molecule in membrane-bound or soluble form, in addition to the membrane-bound fusion protein that includes a non-antibody immunomodulatory molecule operatively fused to a heterologous membrane attachment domain. For example, combinations of cytokines, which can produce an enhanced immune response such as a synergistic response as compared to the response produced by a single cytokine, are particularly useful in the vaccines of the invention. For example, in a vaccine of the invention, GM-CSF can be used in combination with IL-4; IL-1 can be used in combination with TNF, IL-2, G-CSF, GM-CSF or IL-3; or IL-2 can be used in combination with IL-4. Similarly, IL-6 can be used in combination with, for example, IFN-γ, IL-4, IL-2 or M-CSF, and IL-7 can be used in combination with a cytokine such as IL-2 or IL-4 (see Thomson, supra, 1994; Wakimoto et al., *Cancer Vaccine* 56:1828–1833 (1996), which is incorporated herein by reference).

A preferred vaccine of the invention includes GM-CSF in combination with IL-4. Such a cellular vaccine of the invention can include, for example, IL-4 in membrane-bound or soluble form in addition to a membrane-bound fusion protein that contains GM-CSF operatively fused to a heterologous membrane attachment domain. Such a cellular vaccine of the invention also can have GM-CSF in membrane-bound or soluble form in addition to a membrane-bound fusion protein that contains IL-4 operatively fused to a heterologous membrane attachment domain.

In addition, a vaccine of the invention can contain, if desired, a B7-1 (CD80) or B7-2 (CD86) costimulatory molecule or a CD40 or CD40 ligand (Chen et al., *Cell* 71:1093–1102 (1992); Chen et al., *J. Exp. Med.* 179:523–532 (1994); Li et al., *J. Immunol.* 153:421–428

(1994); and Yang et al., *J. Immunol.* 154:2794–2800 (1995), each of which are incorporated herein by reference). A vaccine having a B7-1 or B7-2 costimulatory molecule in addition to a membrane-bound fusion protein including a non-antibody immunomodulatory molecule, such as GM-CSF, IL-2, IFN-γ or IFN-α, operatively fused to a heterologous membrane attachment domain.

The present invention also provides a method of modulating an immune response against a disease-associated antigen. In a method of the invention, an individual is administered a vaccine including a cell having a disease-associated antigen or immunogenic epitope thereof and a non-antibody immunomodulatory molecule operatively fused to a heterologous membrane attachment domain. The methods of the invention can be used alone, for example, to protect against or treat tumors, or can be used as adjuvant therapy following debulking of a tumor by conventional treatment such as surgery, radiotherapy and chemotherapy.

The methods of the invention for modulating an immune response can be used to treat a variety of diseases, conditions and disorders including tumors and cancers, autoimmune diseases, infectious diseases and disorders of bacterial, parasitic or viral etiology. In one embodiment, the methods of the invention can be used to modulate an immune response for protection against or treatment of cancer, including cancers such as melanoma, colorectal cancer, prostate cancer, breast cancer, ovarian cancer, cervical cancer, endometrial cancer, glioblastoma, renal cancer, bladder cancer, gastric cancer, pancreatic cancer, neuroblastoma, lung cancer, leukemia and lymphoma. The methods of the invention also can be used to protect against or treat infectious diseases such as Acquired Immunodeficiency Syndrome (AIDS).

In addition, the methods of the invention can be used to protect against the development of or to treat existing autoimmune diseases such as rheumatoid arthritis, psoriasis, multiple sclerosis, systemic lupus erythematosus and Hashimoto's disease, type I diabetes mellitus, myasthenia gravis, Addison's disease, autoimmune gastritis, Graves' disease and vitiligo. Allergic reactions, such as hay fever, asthma, systemic anaphylaxis or contact dermatitis also can be treated using the methods of the invention for modulating an immune response.

A variety of diseases or conditions of bacterial, parasitic, yeast or viral etiology also can be prevented and treated using the methods of the invention for modulating an immune response. Such diseases and conditions include gastritis and peptic ulcer disease; periodontal disease; Candida infections; helminthic infections; tuberculosis; Hemophilus-mediated disease such as bacterial meningitis; pertussis virus-mediated diseases such as whooping cough; cholera; malaria; influenza infections; respiratory syncytial antigens; hepatitis; poliomyelitis; genital and non-genital herpes simplex virus infections; rotavirus-mediated conditions such as acute infantile gastroenteritis and diarrhea; and flavivirus-mediated diseases such as yellow fever and encephalitis.

As disclosed herein, the methods of the invention can be used to treat an individual having one of such diseases or conditions or an individual suspected of having one of such diseases or conditions. The methods of the invention also can be used to protect an individual who is at risk for developing one of such diseases or conditions from the development of the actual disease. Individuals that are predisposed to developing particular diseases, such as particular types of cancer, can be identified using methods of genetic screening (see, for example, Mao et al., *Canc. Res.* 54(Suppl.):1939s–1940s (1994); Garber and Diller, *Curr. Opin. Pediatr.* 5:712–715 (1993), each of which is incorporated herein by reference). Such individuals can be predisposed to developing, for example, melanoma, retinoblastoma, breast cancer or colon cancer or disposed to developing multiple sclerosis or rheumatoid arthritis.

Immunomodulatory molecules useful in the methods of the invention include immunostimulatory and immunosuppressive molecules such as cytokines and heat shock proteins. A cytokine useful in the methods of the invention can be, for example, GM-CSF, G-CSF, IFN-γ, IFN-α, TNF-α, TNF-β, IL-1. IL-2, IL-3, IL-4, IL-6, IL-7, IL-10, IL-12, lymphotactin or DC-CK1, another of the cytokines described hereinabove, or another cytokine molecule known in the art. Granulocyte macrophage colony stimulating factor (GM-CSF) is particularly useful in the methods of the invention.

Cells useful in the methods of the invention include prokaryotic and eukaryotic cells such as fibroblasts and tumor cells. As described above, a useful tumor cell can be, for example, a melanoma cell, renal carcinoma cell, neuroblastoma cell, glioblastoma cell, lung cancer cell, colon cancer cell, breast cancer cell, prostate cancer cell, bladder carcinoma cell or plasmacytoma cell. In the methods of the invention, a cell can be autologous, allogeneic or xenogeneic to the individual to whom the vaccine is administered. For treatment of humans, allogeneic cells include HLA matched as well as unmatched cells. By HLA matched cells, it is meant that one or more of the major histocompatibility complex molecules on the vaccine cell is the same as one or more of the MHC molecules on cells the individual administered the vaccine cells. Such HLA matched allogeneic cells include, for example, HLA-A2 matched cells.

A variety of disease-associated antigens can be used to modulate an immune response against a disease-associated antigen. As discussed above, a disease-associated antigen can be endogenous or exogenous to the cell having the membrane-bound fusion protein. Such a disease-associated antigen can be, for example, a tumor-associated antigen, autoimmune disease-associated antigen, infectious disease-associated antigen, viral antigen, parasitic antigen or bacterial antigen. Tumor-associated antigens include p53 and mutants thereof, Ras and mutants thereof, a Bcr/Abl breakpoint peptide, HER-2/neu, HPV E6, HPV E7, carcinoembryonic antigen, MUC-1, MAGE-1, MAGE-3, BAGE, GAGE-1, GAGE-2, N-acetylglucosaminyltransferase-V, p15, gp100, MART-1/MelanA, tyrosinase, TRP-1, β-catenin, MUM-1 and CDK-4. Autoimmune disease-associated antigens include, for example, T cell receptor derived peptides. If desired, the disease-associated antigen or immunogenic epitope thereof can be operatively fused to the membrane-bound fusion protein.

The number of vaccine cells to be administered to an individual according to a method of the invention is the number of cells that can modulate an immune response against a disease-associated antigen. An effective number of vaccine cells to be administered can be determined using an assay for determining the activity of immunoeffector cells following administration of the vaccine to the individual or by monitoring the effectiveness of the therapy using well known in vivo diagnostic assays as described below. In general, a vaccine containing approximately $1 \times 10^4$ to $1 \times 10^8$ cells, and preferably $1 \times 10^7$ to $1 \times 10^8$ cells, is useful for modulating an immune response. One skilled in the art understands that the number of vaccine cells to be administered depends, for example, on the number of times the vaccine is to be administered and the level of response desired.

The vaccine cells of the invention can be administered with a pharmacologically acceptable solution such as physiological saline or with an appropriate adjuvant. Numerous pharmalogically acceptable solutions and adjuvants useful for immunization are known within the art. It is recognized that the vaccine cells of the invention should be stable in such solutions or adjuvants; for example, pharmacologically acceptable solutions which result in cell lysis are not useful in the methods of the invention.

Vaccine administration can be accomplished by any of various methods including subcutaneous, intradermal or intramuscular injection, injection directly into tumor lesions, and oral administration. One skilled in the art understands that oral administration is particularly useful for prokaryotic vaccines such as Salmonella vaccines. Intradermal or subcutaneous administration, or a combination thereof, is particularly useful for administration of a vaccine containing membrane-bound GM-CSF. For treatment of tumors, administration can be at the site of a tumor or can be at a location other than the primary tumor site. Multiple routes of administration, as well as administration at multiple sites to increase the area contacted by the vaccine, also are envisioned by the present invention. It is recognized that booster vaccines administered, for example, every several months, also can be useful in modulating an immune response against a disease-associated antigen according to a method of the invention.

One skilled in the art would know that the effectiveness of therapy can be determined by monitoring immune functions in the patient. In anti-tumor therapy, for example, the cytolytic activity of immune effector cells against a patient's cancer cells can be assayed using the methods described in Example II. In addition, the size or growth rate of a tumor can be monitored in vivo using methods of diagnostic imaging. By monitoring the patient during therapy, the physician would know whether to use repeated administration of a vaccine of the invention.

Further provided herein is a nucleic acid molecule including a nucleotide sequence encoding an non-antibody immunomodulatory molecule operatively linked to a heterologous nucleotide sequence encoding a membrane attachment domain functional at neutral or basic pH. The non-antibody immunomodulatory molecule can be an immunostimulatory or immunosuppressive molecule. Cytokines and heat shock proteins, for example, are immunomodulatory molecules useful in the nucleic acid molecules of the invention. Such a cytokine can be, for example, GM-CSF, G-CSF, IFN-γ, IFN-α, TNF-α, TNF-β, IL-1. IL-2, IL-3, IL-4, IL-6, IL-7, IL-10, IL-12, lymphotactin and DC-CK1. The cytokine GM-CSF is particularly useful in the nucleic acid molecules of the invention.

A nucleic acid molecule including a nucleotide sequence encoding an non-antibody immunomodulatory molecule operatively linked to a heterologous nucleotide sequence encoding a membrane attachment domain functional at neutral or basic pH can further include, if desired, an operatively linked nucleotide sequence encoding a disease-associated antigen or immunogenic epitope thereof.

Nucleic acids encoding cytokine-diphtheria toxin fusion proteins have been previously described (vanderspek et al, *Mol. Cell. Biochem.* 138:151–156 (1994); Murphy and vanderSpek, *Seminars Cancer Biol.* 6: 259–267 (1995), each of which are incorporated herein by reference). These fusion proteins contain a hydrophobic domain of diphtheria toxin, which function at acidic pH in delivery from endocytic vesicles to the cytosol. However, such diphtheria toxin hydrophobic domains do not function at neutral pH, for example, in membrane binding to a plasma membrane. Thus, nucleic acids encoding diphtheria toxin fusion proteins are excluded from the nucleic acids of the invention.

The disease-associated antigen can be, for example, a tumor-associated antigen, autoimmune disease-associated antigen, infectious disease associated antigen, viral antigen, parasitic antigen or bacterial antigen. Tumor-associated antigens include p53 and mutants thereof, Ras and mutants thereof, Bcr/Abl breakpoint peptides, HER-2/neu, HPV E6, HPV E7, carcinoembryonic antigen, MUC-1, MAGE-1, MAGE-3, BAGE, GAGE-1, GAGE-2, N-acetylglucosaminyltransferase-V, p15, gp100, MART-1/ MelanA, tyrosinase, TRP-1, β-catenin, MUM-1 and CDK-4 as well as other tumor-associated antigens known in the art. Autoimmune disease-associated antigens include, for example, T cell receptor derived peptides.

The invention further provides a nucleic acid molecule including a nucleotide sequence encoding a non-antibody immunomodulatory molecule operatively linked to a heterologous nucleotide sequence encoding a membrane attachment domain, provided that the membrane attachment domain is not derived from diphtheria toxin.

The following examples are intended to illustrate but not limit the present invention.

EXAMPLE I

Production of Cellular Vaccines Containing Membrane-bound GM-CSF

This example describes the preparation and use of a cellular vaccine including a membrane-bound GM-CSF fusion protein.

Preparation of the pHOOK™-1.GM-CSF Expression Construct

In order to isolate the mouse GM-CSF CDNA, total RNA was prepared from Concanavalin A-stimulated spleen cells isolated from Balb/c mice (Jackson Labs, Bar Harbor, Me.). Stimulated spleen cells were lysed in TriZol™ (Gibco-BRL; Gaithersburg, Md.) at a concentration of $5 \times 10^6$ cells/ml Trizol™ and frozen at −70° C. Cells were then thawed, 200 µl chloroform added and the sample vortexed 15–30 seconds. The sample was then incubated at room temperature for 10 minutes before centrifuging at 12,000×g for 15–20 minutes at 4° C. The colorless aqueous phase was removed to a new tube, and 5–20 µl of glycogen added from a stock solution of 20 µg/µl. After adding 500 µl isopropyl alcohol, the sample was incubated for 1 hour at 15°–30° C. and then centrifuged at 12,000×g for 10 minutes at 4° C. The supernatant was removed, and the pellet washed with 1 ml of 75% ethanol by vortexing and subsequently centrifuging at 7,5000×g for 5 minutes at 4° C. The washed pellet was then air dried for 10 minutes and dissolved in 30 µl water.

cDNA synthesis was performed using SuperScript™ II (Gibco-BRL) essentially as follows. Briefly, oligo dT primers (0.5 µg) were added to 2.5 µg RNA sample. The volume was adjusted to 11 µl with water, and the samples incubated at −70° C. for 10 minutes, before placing on ice for at least 1 minute. The following mixture was prepared and added to the sample: 2 µl 10X PCR buffer from SuperScript™ II kit; 2 µl 25 mM MgCl$_2$; 1 µl 10 mM dNTP; and 2 µl 0.1M DTT. The mixture was incubated at 42° C. for 5 minutes before the addition of 1 µl (200 units) SuperScript™ II reverse transcriptase and a further incubation at 42° C. for 50 minutes. The reaction was stopped by incubation for 15 minutes at −70° C., followed by chilling on ice. After centrifuging briefly, the mixture was incubated with RNAseH for 20 minutes at 37° C., and the volume adjusted to 100 µl with water.

Murine GM-CSF was amplified essentially as follows. The 5' PCR murine GM-CSF primer SEQ ID NO:47 contains an ApaI restriction site and has the sequence 5'-GCGGAGGGGCCCTAGCACCCACCCGCTCACCCA-TCACT-3'. The 3' PCR murine GM-CSF primer SEQ ID NO:8 contains a SalI restriction site and has the sequence 5'-ACCGCGGTCGACTTTTTGGACTGGTTTTTTGCAT-TCAAAGGGG-3'. These GM-CSF specific primers were used in a reaction containing 5 μl of 10 μM stocks of each GM-CSF primer; 2 μl of GM-CSF cDNA isolated from Concanavalin A-stimulated mouse spleen cells; 4 μl 10 mM cDNA (Gibco-BRL); 10 μl 10X Taq polymerase buffer (Perkin Elmer); 10 μl 25 mM MgCl$_2$; and 69 μl water. The sample was heated to 100° C. for 5 minutes, cooled to 80° C. and incubated for 5 minutes before adding 2 units of Taq polymerase. The sample was then amplified in a Perkin Elmer Cetus DNA thermocycler for 35 cycles with an annealing temperature of 55° C.

Figure 1B:
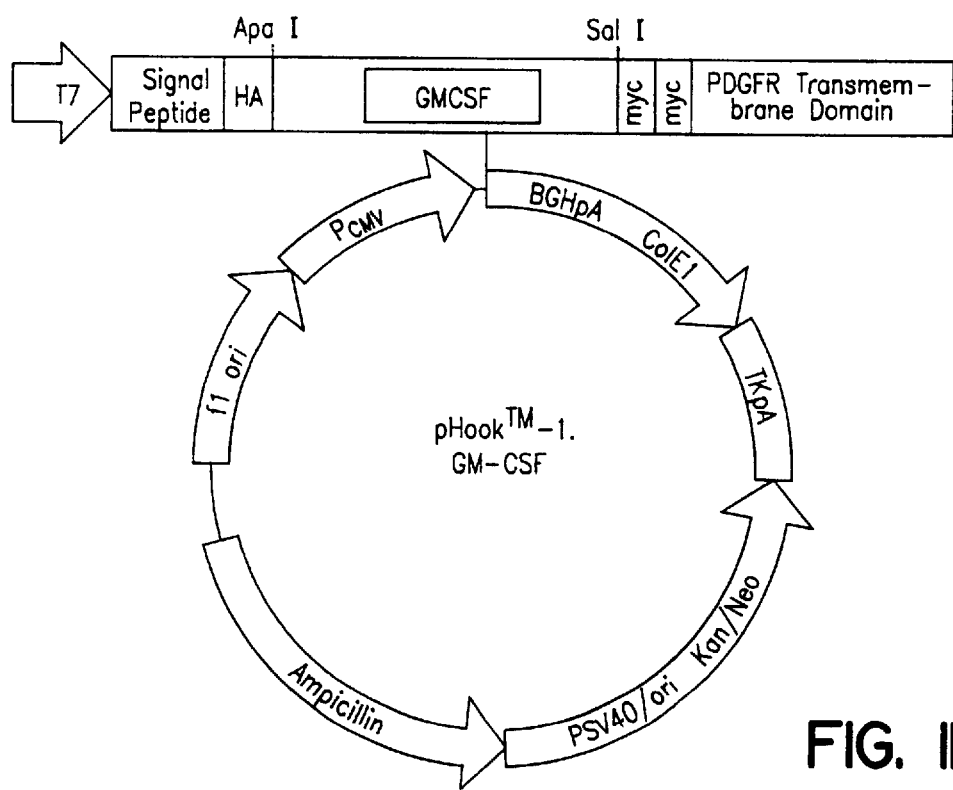

As shown in FIG. 1, the pHOOK™-1 vector (Invitrogen, San Diego, Calif.) contains the coding sequence for a single-chain antibody located between the murine kappa chain signal peptide and a platelet-derived growth factor receptor (PDGFR) membrane attachment domain coding sequence. The pHOOK™-1 vector also contains sequences coding for ampicillin, kanamycin and neomycin resistance. The murine GM-CSF PCR fragment was purified and cloned into the ApaI and SalI sites of pHOOK™-1 to produce pHOOK™-1.GM-CSF. JM109 cells were transformed with the ligation mixture, and restriction digest analysis subsequently used to identify clones that were positive for the GM-CSF insert. A large-scale preparation of endotoxin-free pHOOK™-1.GM-CSF plasmid material was prepared using the Qiagen plasmid purification system (Qiagen, Chatsworth, Calif.) according to the manufacturer's instructions. A control construct for expression of soluble GM-CSF was prepared similarly but contains a stop codon prior to the SalI site.

Transfections and Clone Selection

Mouse colon adenocarcinoma CT-26 cells were obtained from the Sidney Kimmel Cancer Center (SKCC, La Jolla, Calif.) and are described in Fakhrai et al., *Human Gene Therapy* 6:591–601 (1995) and Shawler et al., *J. Immunol. Emphasis Tumor Immunol.* 17:201–208 (1995), each of which are incorporated herein by reference. The CT-26 cells were transfected by electroporation using Superfect (Qiagen) according to the manufacturer's instructions. Clones were selected with 1 mg/ml G418 (Gibco-BRL) in RPMI 1640 media supplemented with 10% fetal bovine serum (FBS), penicillin-streptomycin, L-glutamic acid and β-mercaptoethanol. Transfected cell lines were maintained in selective media.

Reverse Transcriptase Polymerase Chain Reaction

Figure 3:
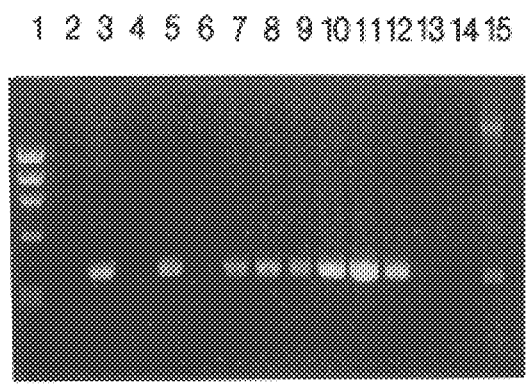
FIG. 3 shows analysis of GM-CSF expression in pHOOK™-1.GM-CSF CT-26 cell transfectants using reverse transcriptase polymerase chain reaction (RT-PCR). Lane 1: ΦX174 molecular weight markers. Lanes 2 through 13: CT-26 pHOOK™-1.GM-CSF transfectants A3, A5, A6, B4, B5, C2, C3, C4, C5, C6, D3 and D5. Lane 14: untransfected CT-26 cells. Lane 15: Concanavalin A stimulated Balb/c spleen cells.
Figure 4A:
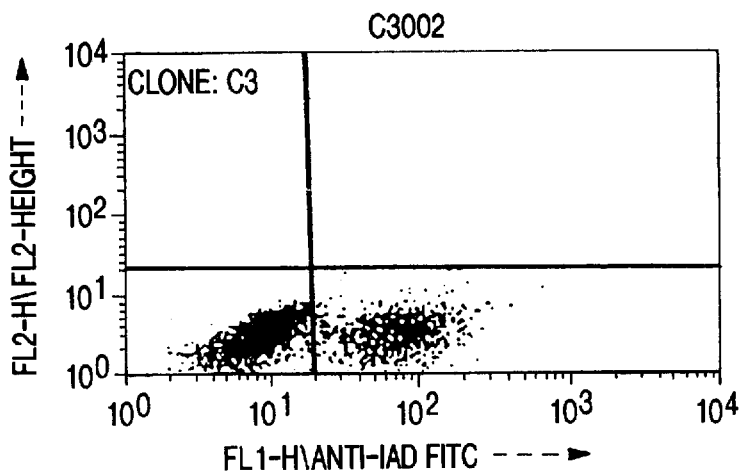
FIGS. 4A–4D show exemplary double stain FACS analysis of the "C3" pHOOK™-1.GM-CSF transfected clone.
Figure 4B:
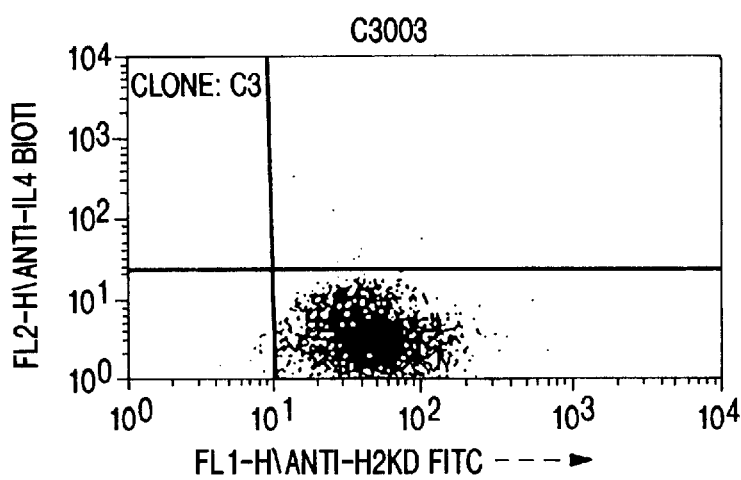
Figure 4C:
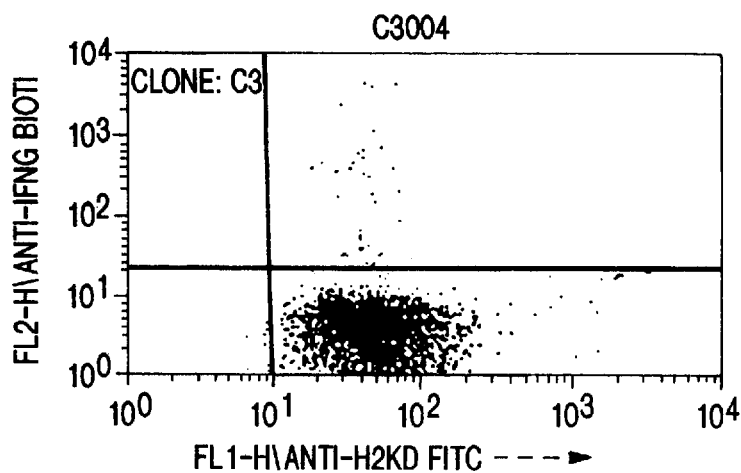
Figure 4D:
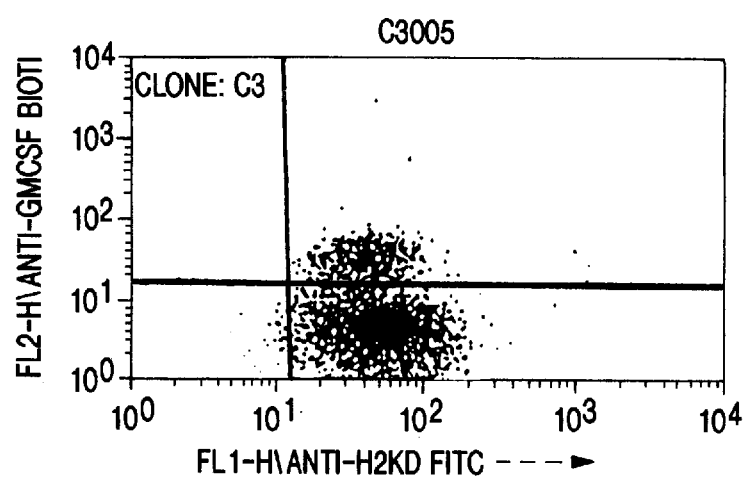

Cells expressing membrane-bound GM-CSF by FACS were further analyzed for the presence of GM-CSF mRNA by RT-PCR as described above. RNA was prepared with TriZol™ (Gibco-BRL), and CDNA was isolated as described in the product protocol. Primers SEQ ID NOS:47 and 48, described above, amplify a fragment of 370 bp from the pHOOK™-1.GM-CSF template. As shown in FIG. 3, of twelve G418-resistant CT-26 transfectants, eight had the 370 bp PCR amplified fragment, indicating that these lines were positive for GM-CSF mRNA. The 370 bp fragment indicative of GM-CSF mRNA is evident in the positive control Concanavalin A stimulated Balb/c spleen cells, but absent from wild type CT-26 cells as expected.

Flow Cytometry

After 4 weeks of selection in G418 containing media, colonies positive for GM-CSF mRNA were screened for the expression of membrane-bound GM-CSF by flow cytometry on a Becton Dickinson FACSTAR (Becton Dickinson, San Jose, Calif.). Briefly, cells were harvested and washed in 1% FBS in phosphate-buffered saline (PBS) and incubated with anti-GM-CSF fluorescein-labeled monoclonal antibody (Pharmingen, La Jolla, Calif.) for 1 hour on ice. The cells were washed with 1% FBS in PBS and analyzed for expression of membrane-bound GM-CSF. Of eight G418 resistant lines having murine GM-CSF mRNA by RT-PCR analysis, six were shown by fluorescence activated cell sorting (FACS) to have cell surface expressed GM-CSF.

Double Stain FACS Analysis of pHOOK™-1.GM-CSF Transfected CT-26 Cells

The staining of transfected cells with antibodies specific for GM-CSF was performed essentially as described above, with the addition of a simultaneous staining antibody control for various markers (anti-H-2K$^d$ class I MHC marker, anti-IFN-γ, anti-I-A$^d$ class II MHC marker).

The results of several of the transfected clones demonstrated a positive staining with the anti-GM-CSF antibody, while antibodies against other marker proteins were negative. The positive control anti-H-2K$^d$ antibody showed a positive signal on all pHOOK™-1.GM-CSF transfected CT-26 cells at the same magnitude as the wild-type controls. The negative control anti-IFN-γ and anti-I-A$^d$ antibodies were significantly lower or negative on all cells.

Representative FACS analysis of the pHOOK™-1.GM-CSF CT-26 transfectant "C3" is shown in FIG. 4. Staining with anti-H-2K$^d$ antibody, shown along the X-axis of panels B, C, and D, yielded a positive signal as expected for this positive control antibody. Staining with anti-IL-4 is shown along the Y axis of panel B, and staining with anti-IFN-γ is shown along the Y axis of panel C. As shown in these panels, the PHOOK™-1.GM-CSF transfected CT-26 cells did not express cell-surface IL-4 or IFN-γ. However, as shown in panel D, staining with anti-GM-CSF was positive. These results demonstrate that GM-CSF is expressed on the cell surface of pHOOK™-1.GM-CSF transfected cells.

Radioimmunoprecipitation Assay

Surface expression of GM-CSF is further assayed by surface iodination and immunoprecipitation of pHOOK™-1.GM-CSF transfected cells essentially as described in Kranz et al., *Proc. Natl. Acad. Sci., USA* 81:573–577 (1984), which is incorporated herein by reference. Briefly, transfected cells are surface iodinated with Iodo-Beads® (Pierce Chemicals, Rockford, Ill.) according to the manufacturer's instructions. After anti-GM-CSF antibody (Pharmingen) is conjugated to Affi-gel® (BioRad Laboratories, Richmond, Calif.), the conjugated Affi-gel® beads are incubated with the iodinated cells for one hour on ice. Subsequently, the mixture is incubated with Triton X-100 to a final concentration of 0.1% for a further 15 minutes on ice.

To remove unbound proteins, the Affi-gel® beads are washed five times with ice cold 1% FBS in PBS. SDS loading dye is added to the washed beads, and the mixture heated to 100° C. for 2 minutes. The immunoprecipitated products are analyzed by electrophoresis on a 15% SDS-PAGE gel, which is dried and analyzed by autoradiography.

CT-26 transfectants expressing membrane-bound GM-CSF/PDGFR fusion protein have a labeled protein of about 20 kDa. This protein is absent from the negative control, wild type CT-26 cells.

Bone Marrow Proliferation Assay

In order to test membrane-bound GM-CSF for biological activity, pHOOK™-1.GM-CSF transfected CT-26 cells are assayed for the ability to stimulate proliferation of fresh bone marrow cells as described in Bulkwill (Ed), *Cytokines:*

A Practical Approach Oxford Press (1995) pp 247–268, which is incorporated herein by reference. Briefly, pHOOK™-1.GM-CSF transfected CT-26 cells or control non-transfected CT-26 cells ($2 \times 10^5$ cells per well) are incubated with an equal number of syngeneic mouse bone marrow cells in 96-well plates. After two days, wells are pulsed with 1 μCi of $^3$H-thymidine and incubated for another day. The cells are harvested onto filters using a vacuum manifold, and the amount of $^3$H-thymidine subsequently analyzed. Bone marrow proliferation, as indicated by the amount of $^3$H-thymidine, is significantly greater for cells incubated with pHOOK™-1.GM-CSF transfected CT-26 cells as compared to non-transfected CT-26 cells.

EXAMPLE II

Tumor Protection Using Cellular Vaccines Containing Membrane-bound GM-CSF

This example demonstrates that a cellular vaccine expressing a membrane-bound GM-CSF/PDGFR fusion protein can be used for tumor protection.

Tumor Protection Experiments pHOOK™-1.GM-CSF transfected CT-26 cells are assayed for the ability to protect mice inoculated with wild type CT-26 colon adenocarcinoma cells essentially as described in Shawler et al., *J. Immunol. Emphasis Tumor Immunol.* 17:201–208 (1995), which is incorporated herein by reference. Briefly, pHOOK™-1.GM-CSF transfected CT-26 cells are irradiated with 25,000 rads using a JLShepard and Associates Model 109-85 Irradiator with a $^{60}$Cobalt source. Balb/c mice (Jackson Labs) are vaccinated with $1 \times 10^4$ irradiated pHOOK™-1.GM-CSF transfected CT-26 cells and boosted twice weekly with $1 \times 10^4$ cells. Subsequently, mice are challenged with $1 \times 10^4$ live, wild type CT-26 cells in the opposite flank. Tumor dimensions are scored every other day to evaluate the efficacy of the vaccine.

The pHOOK™-1.GM-CSF transfected CT-26 vaccine cells significantly reduce tumor growth as compared to animals vaccinated with wild-type CT-26 cells and as compared to unvaccinated animals. In addition, the pHOOK™-1.GM-CSF transfected CT-26 vaccine cells significantly reduce tumor growth as compared to animals vaccinated with CT-26 cells producing a soluble form of murine GM-CSF.

Cytotoxic T Lymphocyte Assays

Spleens are removed from mice vaccinated and boosted with irradiated pHOOK™-1.GM-CSF transfected CT-26 cells. In order to detect the presence of cytotoxic T lymphocytes specific for CT-26 tumor cells, a single cell suspension is made from the spleens and used as the effector cells in a standard 4 hour chromium release assay (Kranz et al., *Proc. Natl. Acad. Sci. USA* 81:7922–7926 (1984), which is incorporated herein by reference). Briefly, the target cells are wild type CT-26 cells that are passively labeled with 125 μCi $^{51}$Cr in complete medium for 1 hour in a 37° C. water bath. The CT-26 target cells are washed 3 times in complete media and incubated with increasing numbers of spleen cells from vaccinated animals for 4 hours in a 5% $CO_2$ humidified incubation chamber. The percent specific lysis (chromium release) is calculated as $$100\% \times (cpm_{experimental} - cpm_{spontaneous})/(cpm_{maximal} - cpm_{spontaneous}),$$

T Cell Proliferation Assays

Vaccinated animals are assayed for an increased population of T cells that are specific for wild-type CT-26 cells. Essentially, spleens of vaccinated animals are removed, and a single cell suspension prepared as described above. Approximately $2 \times 10^5$ spleen cells are incubated with increasing numbers of irradiated, wild-type CT-26 cells for 3 days in 5% $CO_2$ at 37° C. On day 2, the cells are pulsed with 1 μCi of $^3$H-thymidine. The cells are harvested onto glass fiber filters, and the amount of $^3$H-thymidine counted. The amount of stimulation (stimulation index) is calculated as the amount of $^3$H-thymidine of the experimental wells divided by the amount of $^3$H-thymidine of T cells exposed only to complete media.

ELISAs and FACS Analysis of Serum Antibodies

Vaccinated animals are assayed for the ability to elicit specific antibodies to CT-26. Vaccinated animals are bled retro-orbitally to obtain serum. The serum is diluted 1:50, 1:100 and 1:500 and incubated with whole wild-type CT-26 cells. The cells are subsequently washed 2 times with cold PBS containing 1% BSA and incubated with a FITC-conjugated secondary antibody specific for mouse immunoglobulin. The cells are washed once more and analyzed by FACS for staining.

For ELISA assays, CT-26 cells are fixed with glutaraldehyde in a 96-well plate format and washed with PBS containing 1% BSA. The fixed cell monolayer is subsequently blocked with PBS containing 1% BSA for 1 hour at room temperature. The cells are stained with diluted antisera from vaccinated animals for 1 hour at room temperature. After washing with blocking buffer, HRP-conjugated goat anti-mouse Ig secondary antibody is added for 1 hour at room temperature. The secondary reagent is washed, and the fixed cells reacted with HRP substrate (Kirkegaard and Perry Labs, Bethesda, Md.).

All journal article, reference, and patent citations provided above, in parentheses or otherwise, whether previously stated or not, are incorporated herein by reference.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A pharmaceutical composition, comprising a cell having a membrane bound fusion protein comprising Granulocyte Macrophage-Colony Stimulating Factor (GM-CSF) fused to a heterologous membrane attachment domain, said cell further comprising a disease-associated antigen or immunogenic epitope thereof.

2. The pharmaceutical composition of claim 1, wherein said cell is a prokaryotic cell.

3. The pharmaceutical composition of claim 1, wherein said cell is a eukaryotic cell.

4. The pharmaceutical composition of claim 3, wherein said eukaryotic cell is a fibroblast.

5. The pharmaceutical composition of claim 3, wherein said eukaryotic cell is a tumor cell.

6. The pharmaceutical composition of claim 5, wherein said tumor cell is selected from the group consisting of melanoma cell, renal carcinoma cell, neuroblastoma cell, glioblastoma cell, lung cancer cell, colon tumor cell, breast tumor cell, prostate tumor cell, bladder carcinoma cell and plasmacytoma cell.

7. The pharmaceutical composition of claim 1, wherein said disease-associated antigen is endogenous to said cell.

8. The pharmaceutical composition of claim 1, wherein said disease-associated antigen is exogenous to said cell.

9. The pharmaceutical composition of claim 1, wherein said disease-associated antigen is selected from the group consisting of tumor-associated antigen, autoimmune disease-associated antigen, infectious disease-associated antigen, viral antigen, parasitic antigen and bacterial antigen.

10. The pharmaceutical composition of claim 9, wherein said tumor-associated antigen is selected from the group consisting of p53 and mutants thereof, Ras and mutants thereof, a Bcr/Abl breakpoint peptide, HER-2/neu, HPV E6, HPV E7, carcinoembryonic antigen, MUC-1, MAGE-1, MAGE-3, BAGE, GAGE-1, GAGE-2, N-acetylglucosaminyltransferase-V, p15, gp100, MART-1/MelanA, tyrosinase, TRP-1, β-catenin, MUM-1 and CDK-4.

11. The pharmaceutical composition of claim 9, wherein said autoimmune disease-associated antigen is a T cell receptor derived peptide.

12. The pharmaceutical composition of claim 10, wherein said disease-associated antigen or immunogenic epitope thereof is fused to said membrane-bound fusion protein.

13. A method of stimulating an immune response against a disease-associated antigen, comprising administering to an individual a pharmaceutical composition comprising a cell having:

(a) a disease-associated antigen or immunogenic epitope thereof; and (b) GM-CSF fused to a heterologous membrane attachment domain;

wherein an immune response is stimulated.

14. The method of claim 13, wherein said cell is a prokaryotic cell.

15. The method of claim 13, wherein said cell is a eukaryotic cell.

16. The method of claim 15, wherein said eukaryotic cell is a fibroblast.

17. The method of claim 15, wherein said eukaryotic cell is a tumor cell.

18. The method of claim 17, wherein said tumor cell is selected from the group consisting of melanoma cell, renal carcinoma cell, neuroblastoma cell, glioblastoma cell, lung cancer cell, colon cancer cell, breast cancer cell, prostate cancer cell, bladder carcinoma cell and plasmacytoma cell.

19. The method of claim 13, wherein said disease-associated antigen is endogenous to said cell.

20. The method of claim 13, wherein said disease-associated antigen is exogenous to said cell.

21. The method of claim 13, wherein said disease-associated antigen is selected from the group consisting of a tumor-associated antigen, autoimmune disease-associated antigen, infectious disease-associated antigen, viral antigen, parasitic antigen and bacterial antigen.

22. The method of claim 21, wherein said tumor-associated antigen is selected from the group consisting of p53 and mutants thereof, Ras and mutants thereof, a Bcr/Abl breakpoint peptide, HER-2/neu, HPV E6, HPV E7, carcinoembryonic antigen, MUC-1, MAGE-1, MAGE-3, BAGE, GAGE-1, GAGE-2, N-acetylglucosaminyltransferase-V, p15, gp100, MART-1/MelanA, tyrosinase, TRP-1, β-catenin, MUM-1 and CDK-4.

23. The method of claim 21, wherein said autoimmune disease-associated antigen is a T cell receptor derived peptide.

24. The method of claim 13, wherein said disease-associated antigen or immunogenic epitope thereof is fused to said membrane-bound fusion protein.

* * * * *

UNITED STATES PATENT AND TRADEMARK OFFICE
CERTIFICATE OF CORRECTION

PATENT NO. : 5,891,432
DATED : Apr. 6, 1999
INVENTOR(S) : Soo Hoo, William

It is certified that error appears in the above-identified patent and that said Letters Patent is hereby corrected as shown below:

The inventor's name is incorrect. The patent inventor is Soo Hoo, William.

The title page, [54], please delete "GM=CSF" and replace therefor with --GM-CSF--

In column 1, in the title, please delete "GM=CSF" and replace therefor with --GM-CSF--.

In column 2, line 58, please delete "amino acid" and replace therefor with --nucleotide--.

In column 2, line 59, please delete "nucleotide" and replace therefor with --amino acid--.

In column 2, line 63, please insert --FIG. 2 also shows the nucleotide sequence (SEQ ID NO:49) and amino acid sequence (SEQ ID NO:50) of the region following the stop codon at nucleotides 658-660.--

In column 5, line 21, please delete "1880-11-884" and replace therefor with --1880-1884--.

UNITED STATES PATENT AND TRADEMARK OFFICE
CERTIFICATE OF CORRECTION

PATENT NO.   : 5,891,432
DATED        : Apr. 6, 1999
INVENTOR(S)  : Soo Hoo, William It is certified that error appears in the above-identified patent and that said Letters Patent is hereby corrected as shown below:

In column 5, line 43, please delete "628918" and replace therefor with --628: 9-18--.

In column 9, line 14, please delete "he" and replace therefor with --the--

In column 11, line 56, please delete "gale" and replace therefor with --galE--.

In column 13, line 45, please delete "within" and replace with --outside--.

In column 16, line 20, please delete "91-21-930" and replace therefor with --921-930--.

In column 17, line 33, please delete "appears increase" and replace therefor with --appears to increase--.

In column 21, line 60, please delete "(vanderspek" and replace therefor with --(vanderSpek--.

UNITED STATES PATENT AND TRADEMARK OFFICE
CERTIFICATE OF CORRECTION

PATENT NO. : 5,891,432
DATED : Apr. 6, 1999
INVENTOR(S) : Soo Hoo, William

It is certified that error appears in the above-identified patent and that said Letters Patent is hereby corrected as shown below:

In column 22, line 34, please delete "CDNA" and replace therefor with --cDNA--.

In column 23, line 6, please delete "8" and replace therefor with --48--.

In column 23, line 55, please delete "CDNA" and replace therefor with --cDNA--.

Claim 12, column 49, line 61, please delete "10" and replace therefor with --1--.

Signed and Sealed this

Eighth Day of May, 2001

*Attest:*

NICHOLAS P. GODICI

*Attesting Officer*     Acting Director of the United States Patent and Trademark Office